US012217833B1

(12) United States Patent
Triana

(10) Patent No.: US 12,217,833 B1
(45) Date of Patent: Feb. 4, 2025

(54) METHOD AND SYSTEM FOR ENHANCING MUSCLE PROTEIN SYNTHESIS PER GRAM OF PROTEIN FOR A PROTEIN SAMPLE

(71) Applicant: The Performance Vibe LLC, Hobe Sound, FL (US)

(72) Inventor: Andrew Triana, Hobe Sound, FL (US)

( * ) Notice: Subject to any disclaimer, the term of this patent is extended or adjusted under 35 U.S.C. 154(b) by 0 days.

(21) Appl. No.: 18/743,592

(22) Filed: Jun. 14, 2024

(51) Int. Cl.
*G16B 45/00* (2019.01)

(52) U.S. Cl.
CPC .................................... *G16B 45/00* (2019.02)

(58) Field of Classification Search
CPC ....................................................... G16B 45/00
USPC ............................................................ 703/11
See application file for complete search history.

(56) References Cited

U.S. PATENT DOCUMENTS

| | | | | |
|---|---|---|---|---|
| 6,195,449 B1 * | 2/2001 | Bogden | ................. | G06V 20/69 382/129 |
| 6,862,532 B2 * | 3/2005 | Yoshida | ................. | G16B 40/00 435/6.19 |
| 10,534,813 B2 * | 1/2020 | Carmeli | ................. | G16H 50/50 |
| 10,546,019 B2 * | 1/2020 | Carmeli | ................. | G16B 45/00 |
| 2002/0172971 A1 * | 11/2002 | Yoshida | ................. | G16B 40/00 435/6.19 |
| 2007/0086979 A1 * | 4/2007 | Chevrier | ................. | A61P 21/00 424/85.1 |
| 2009/0148462 A1 * | 6/2009 | Chevrier | ............ | C07K 16/2887 424/130.1 |
| 2016/0283677 A1 * | 9/2016 | Carmeli | ................. | G16B 5/00 |
| 2018/0089495 A1 * | 3/2018 | Black | ..................... | G06V 10/40 |

* cited by examiner

*Primary Examiner* — Pierre E Elisca
(74) *Attorney, Agent, or Firm* — Derek Fahey, Esq.; The Plus IP Firm, PLLC

(57) ABSTRACT

A system and method for increasing muscle protein synthesis (MPS) relative to another nitrogenous process is disclosed. The method includes obtaining an amino acid profile of a protein sample comprising a plurality of amino acids and the value of the plurality of amino acids are sorted from greatest to least, and plotting the amino acids, on a two-dimensional graph, in descending order based respective values to identify a final five data points of the amino acid profile to define a slope regression tail. The method includes calculating an initial slope value for each of the final five data points, adjusting the amino acid profile algorithmically to generate an adjusted amino acid profile based on a percent difference between a highest initial slope value of said initial slope values and each of the final five data points of the slope regression tail.

19 Claims, 18 Drawing Sheets

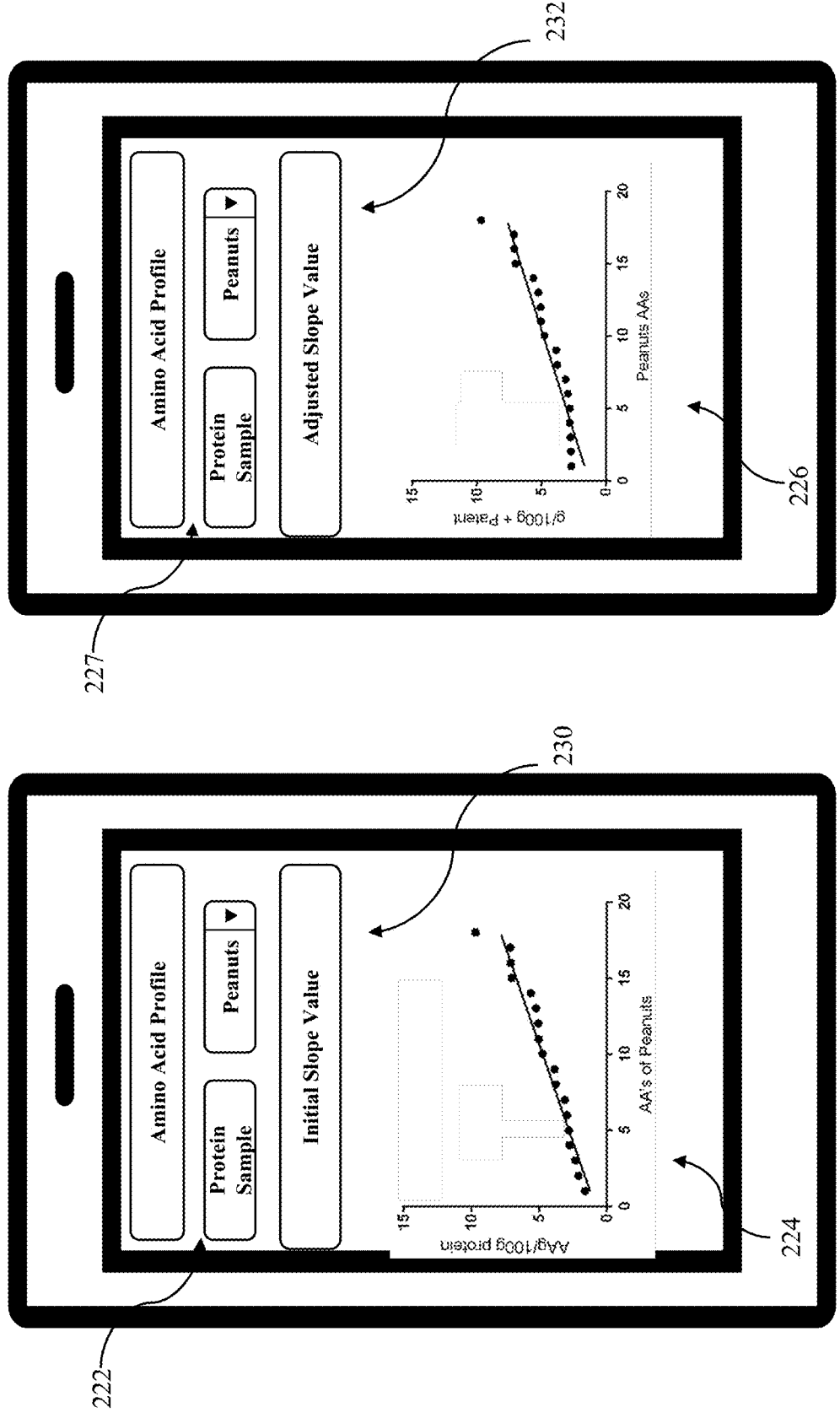

| Amino acid | Whey | Casein | Soy |
|---|---|---|---|
| Alanine | 4.6 | 2.7 | 3.8 |
| Arginine | 2.3 | 3.7 | 6.7 |
| Aspartic acid | 9.6 | 6.4 | 10.2 |
| Cysteine/cystine | 2.8 | 0.3 | 1.1 |
| Glutamic acid | 15.0 | 20.2 | 16.8 |
| Glycine | 1.5 | 2.4 | 3.7 |
| Histidine[a] | 1.6 | 2.8 | 2.3 |
| Isoleucine[a,b] | 4.5 | 5.5 | 4.3 |
| Leucine[a,b] | 11.6 | 8.3 | 7.2 |
| Lysine[a] | 9.1 | 7.4 | 5.5 |
| Methionine[a] | 2.2 | 2.5 | 1.1 |
| Phenylalanine[a] | 3.1 | 4.5 | 4.6 |
| Proline | 4.4 | 10.2 | 4.5 |
| Serine | 3.3 | 5.7 | 4.6 |
| Threonine[a] | 4.3 | 4.4 | 3.3 |
| Tryptophan[a] | 2.3 | 1.1 | 1.1 |
| Tyrosine | 3.3 | 5.7 | 3.3 |
| Valine[a,b] | 4.5 | 6.5 | 4.5 |

FIG. 3C

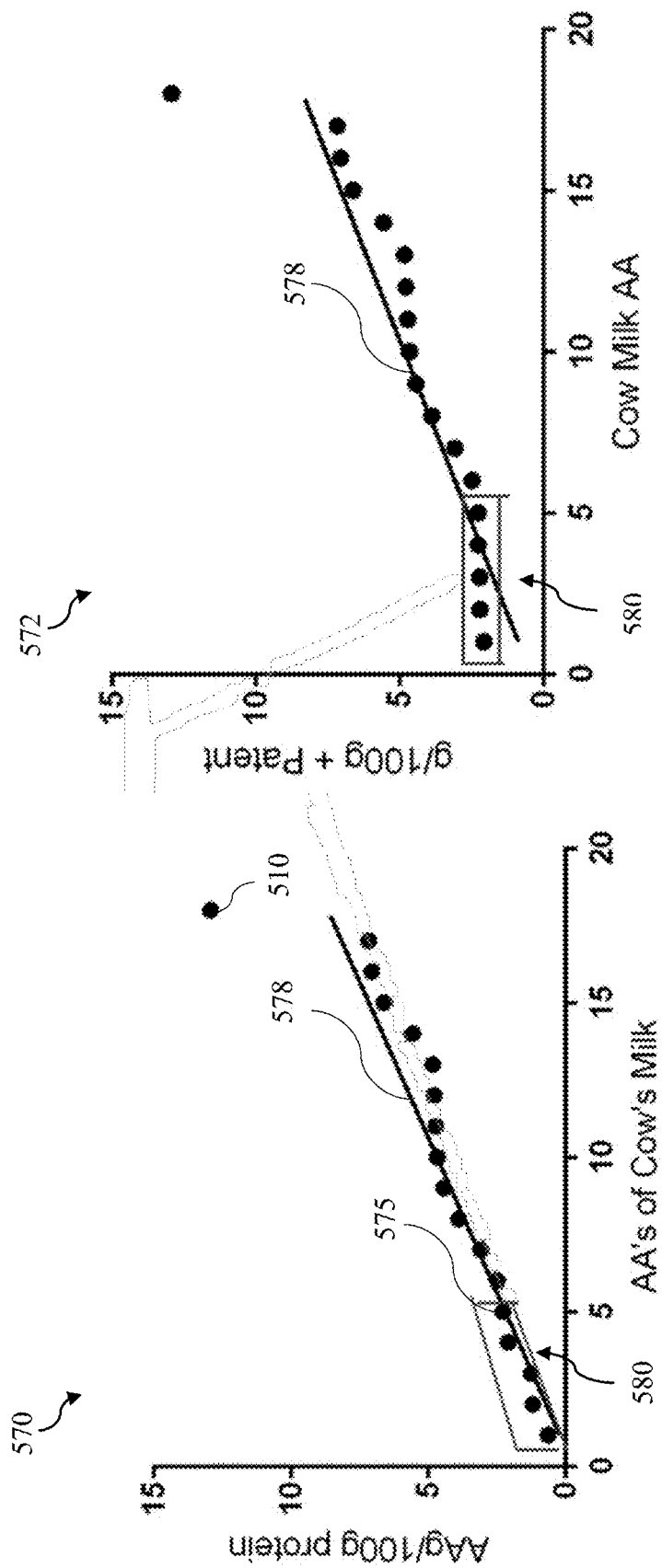

| "O.N-GS100%" + Patent | | SRT Slopes | Peanuts + Patent | | SRT Slopes | Cow's Milk + Patent | | SRT Slopes |
|---|---|---|---|---|---|---|---|---|
| AA Values | Grams | | AA Values | Grams | | AA Values | Grams | |
| Glutamic Acid | 15.12 | | Aspartic Acid | 9.71 | | Glutamic Acid | 12.96 | |
| Aspartic Acid | 9.49 | | Glutamic Acid | 7.15 | | Leucine* | 7.20 | |
| Leucine* | 8.98 | | Tryptophan* | 7.12 | | Proline | 7.08 | |
| Lysine* | 8.69 | | Leucine* | 7.03 | | Lysine* | 6.64 | |
| Threonine* | 5.94 | | Arginine | 5.62 | | Aspartic Acid | 5.58 | |
| Isoleucine* | 5.73 | | Lysine* | 5.25 | | Valine* | 4.89 | |
| Proline | 4.97 | | Valine* | 5.08 | | Isoleucine* | 4.81 | |
| Valine* | 4.74 | | Serine | 5.04 | | Serine | 4.74 | |
| Alanine | 3.96 | | Isoleucine* | 4.77 | | Tyrosine | 4.68 | |
| Serine | 3.90 | | Tyrosine | 3.87 | | Phenylalanine* | 4.46 | |
| Phenylalanine* | 2.60 | | Phenylalanine* | 3.79 | | Threonine* | 3.93 | |
| Tyrosine | 2.54 | | Threonine* | 3.12 | | Arginine | 3.11 | |
| Tryptophan* | 1.92 | | Glycine | 2.96 | | Alanine | 2.59 | |
| Arginine | 1.92 | 0.00% | Histidine* | 2.82 | 0.00% | Histidine* | 2.29 | 0.00% |
| Cysteine | | 2.00% | Alanine | | 2.00% | Methionine* | | 3.00% |
| Methionine* | | 1.00% | Methionine* | | 4.00% | Tryptophan* | | 2.00% |
| Histidine* | | 3.00% | Proline | | 2.00% | Glycine | | 3.00% |
| Glycine | | | Cysteine | | | Cysteine | | |
| Total Added (g/100g): | 0.95 | | Total Added (g/100g): | 2.23 | | Total Added (g/100g): | 3.76 | |

Fig. 6B

METHOD AND SYSTEM FOR ENHANCING MUSCLE PROTEIN SYNTHESIS PER GRAM OF PROTEIN FOR A PROTEIN SAMPLE

REFERENCE TO RELATED APPLICATIONS

Not applicable.

CROSS-REFERENCES

Not applicable.

TECHNICAL FIELD

The present disclosure relates to the field of dietary proteins, and more specifically to the field of enhancing muscle protein synthesis through dietary protein consumption having an improved amino acid profile.

BACKGROUND

Dietary proteins are essential macronutrients composed of amino acids that play a critical role in numerous physiological processes, including the growth, repair, and maintenance of muscle tissue. Upon consumption, these proteins are broken down into their constituent amino acids, which are then utilized in various metabolic pathways. One of the primary benefits of dietary protein is its ability to support muscle protein synthesis (MPS), the process by which the body repairs and builds new muscle fibers. MPS is crucial for muscle growth, recovery, and overall physical performance.

The utilization of dietary protein and its constituents, specifically amino acids, plays a pivotal role in various metabolic processes within the human body. Amino acids, the building blocks of proteins, are fundamental to numerous biological functions. Among the myriad of amino acids present in nature, 21 are recognized as dietary essentials. Chemistry often focuses on 18 major dietary amino acids when evaluating a full gram of protein. Post-consumption, dietary protein utilization can be broadly classified into anabolic and anti-catabolic processes. Anabolic processes lead to the synthesis of muscle proteins, non-muscle proteins, ligands, and Deoxyribonucleic Acid (DNA). Conversely, anti-catabolic processes involve the use of amino acids in ways that prevent tissue breakdown without necessarily contributing to new tissue synthesis. Effective muscle protein synthesis (MPS) requires the presence of all essential amino acid (EAA) constituents. If any EAA is absent, MPS halts, and surplus amino acids (AA) are diverted to other biological processes. Among these amino acids, leucine is particularly critical, serving as a central regulator of MPS.

Muscle protein synthesis is quantified in terms of the amount of phenylalanine (an essential amino acid) utilized over time, typically expressed in milligrams per minute. Increasing the total intake of protein or amino acids generally enhances MPS values. However, surplus amino acids that are not used in MPS are repurposed for other individual roles and various anti-catabolic events. According to Le Chatelier's Chemical Principle, changes in the concentration of a rate-limiting amino acid (RLAA) will directly affect the overall yield of MPS. This principle holds true regardless of whether the amino acids are essential or non-essential, once the RLAA is depleted, MPS ceases.

Essential amino acids are critical because they cannot be synthesized by the body and must be obtained through diet. If the availability of an EAA near the RLAA threshold is insufficient, it can adversely impact MPS rates regardless of the overall protein consumption. Whey protein is noted for its superior MPS response compared to other protein sources, largely due to its higher amino acid content (typically 7-10% more) and the fact that two-thirds of its RLAAs are essential amino acids. Despite these advantages, whey protein also has limitations and does not universally outperform other proteins. The amino acid profiles of proteins exhibit natural wave-like curves when analyzed using slope regression lines. This suggests that the interactions within a protein molecule are highly dynamic and complex and the existing techniques are not able to optimize the amount of amino acids in the protein sample. Class action cases related to "amino spiking" have significantly influenced the evolution of protein supplements. This practice involves adding non-essential amino acids to artificially enhance the protein content on labels, leading to industry-wide changes in product formulations. However, these modifications have not improved muscle protein synthesis (MPS), emphasizing the need for greater transparency and integrity in nutritional labeling.

Existing techniques for enhancing MPS in protein samples are inadequate due to the complex and dynamic interactions within protein molecules. These techniques fail to effectively adjust amino acid quantities, underscoring the need for advanced approaches that can accurately enhance the protein's nutritional and functional attributes, addressing the shortcomings of current practices.

As a result, there exists a need for improvements over the prior art and more particularly for a more efficient way of optimizing and improving the amino acid profile of a protein sample to enhance Muscle Protein Synthesis (MPS).

BRIEF SUMMARY OF THE INVENTION

A system and method for increasing, for a gram of protein, muscle protein synthesis (MPS) relative to another nitrogenous process is disclosed. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

In one embodiment, a method for increasing muscle protein synthesis (MPS) relative to another nitrogenous process is disclosed. The method comprises obtaining an amino acid profile of a protein sample having a plurality of amino acids, wherein each of the plurality of amino acids comprise a value measured in grams and wherein the value of the plurality of amino acids are sorted from greatest to least. The method comprises plotting each of the plurality of amino acids, on a two-dimensional graph, in descending order based respective values so as to identify a final five data points of the amino acid profile to define a slope regression tail. This five data points are subset of the amino acids. The method further includes calculating an initial slope value for each of the final five data points, wherein the initial slope value is defined as $M=(Y2-Y1)/(X2-X1)$, with Y representing each value for each of the final five data points and X representing, in the descending order, each of the final five data points. Further, the method comprises adjusting the amino acid profile algorithmically to generate an adjusted amino acid profile, by calculating, for each of the final five data points, a percent difference between a highest initial slope value of said initial slope values and each of the final five data points of the slope regression tail, and multiplying the percent difference by each respective initial slope value to yield a product for each of the final five data points. The method further comprises adding the product back to the value of the respective amino acid to yield a corrected weight for each of the final five data points. For a lowest three amino acids of the plurality of amino acids of the slope regression tail, the method comprises adding a correction score of 1%, 2%, and 3% respectively, by multiplying the corrected weight for each of the lowest three amino acids by the correction score and then subtracting that correction value from the corrected weight.

Additional aspects of the disclosed embodiment will be set forth in part in the description which follows, and in part will be obvious from the description, or may be learned by practice of the disclosed embodiments. The aspects of the disclosed embodiments will be realized and attained by means of the elements and combinations particularly pointed out in the appended claims. It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute part of this specification, illustrate embodiments of the disclosure and together with the description, explain the principles of the disclosed embodiments. The embodiments illustrated herein are presently preferred, it being understood, however, that the disclosure is not limited to the precise arrangements and instrumentalities shown, wherein:

FIGS. 2A, 2B, and 2C are an example embodiment of graphical user interfaces of a first user device, according to an example embodiment;

FIG. 3C illustrates an amino acid profile for various protein samples;

FIGS. 5E and 5F are graphical representations for comparing amino acid profile of another protein sample, according to an example embodiment;

FIGS. 6A and 6B illustrate amino acid profiles for various protein samples, according to an example embodiment;

DETAILED DESCRIPTION

Figure 1:
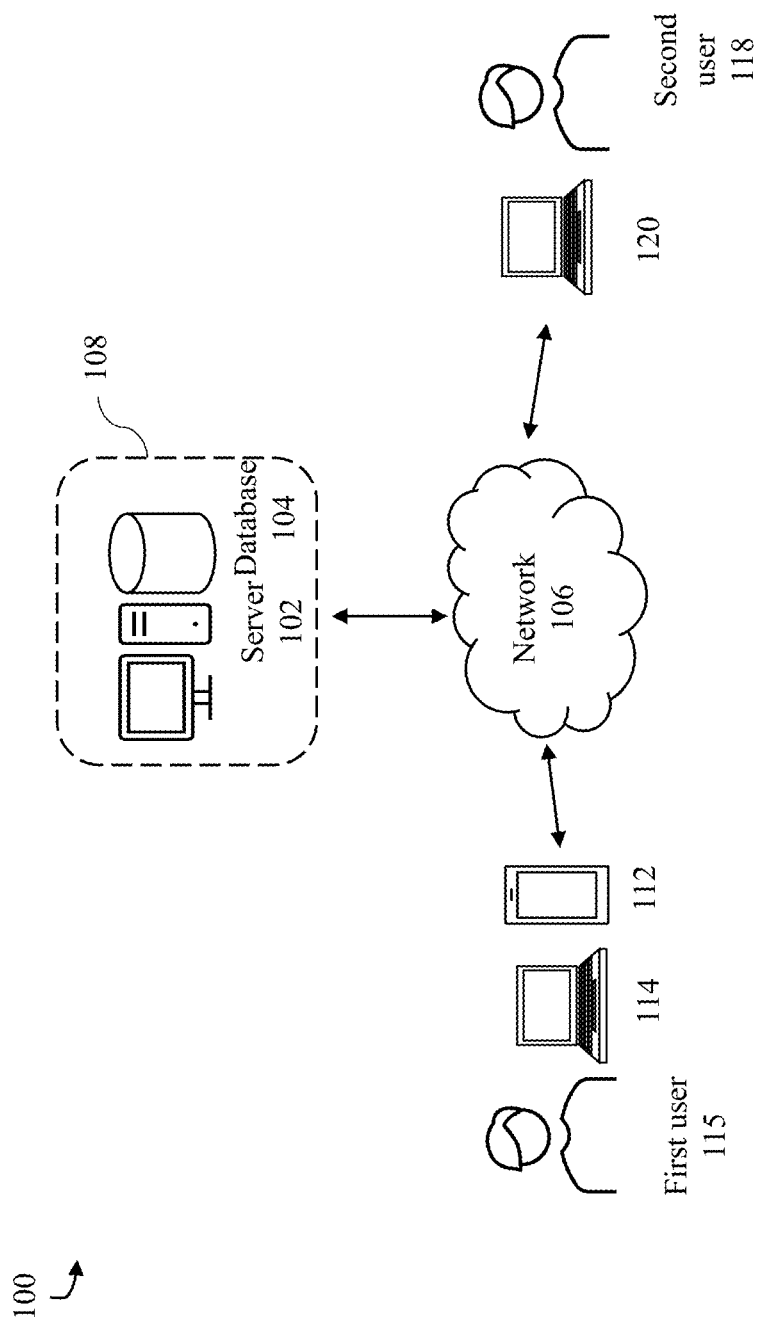
FIG. 1 is a block diagram illustrating a system for increasing muscle protein synthesis (MPS) for protein samples, according to an example embodiment.

The following detailed description refers to the accompanying drawings. Whenever possible, the same reference numbers are used in the drawings and the following description to refer to the same or similar elements. While disclosed embodiments may be described, modifications, adaptations, and other implementations are possible. For example, substitutions, additions, or modifications may be made to the elements illustrated in the drawings, and the methods described herein may be modified by substituting reordering or adding additional stages or components to the disclosed methods and devices. Accordingly, the following detailed description does not limit the disclosed embodiments. Instead, the proper scope of the disclosed embodiments is defined by the appended claims.

The disclosed embodiments improve upon the problems with the prior art by providing a system and method designed to efficiently enhance muscle protein level synthesis in a protein sample. The system uses an efficient algorithm designed to perform precise analysis and optimization of the amino acid profile in the protein sample. This method efficiently improves muscle protein synthesis by accurately determining the weights of amino acids within the sample. The algorithm facilitates targeted adjustments in the amino acid composition, thereby enabling more effective muscle protein synthesis compared to conventional techniques.

The disclosed embodiments improve upon the problems with the prior art by performing analysis based on arranging the amino acids in the protein sample in a decreasing order based on their values by weight, from greatest to least. This ordering places the amino acids with the highest values at the top of the list, followed sequentially by those with lower values. The disclosed embodiments emphasizes those at the bottom of the order. By focusing on and optimizing the values of these lesser-valued amino acids, the current method enhances the overall effectiveness of the protein sample, resulting in a product with improved nutritional properties. This strategic enhancement allows for the tailored improvement of specific amino acids that are often overlooked, thereby broadening the potential applications of the protein in various dietary and therapeutic contexts. Furthermore, this approach ensures a more balanced amino acid profile, which is crucial for achieving optimal health benefits and functional outcomes from protein consumption.

The disclosed embodiments improve upon the prior art by precisely calculating the values of amino acids towards the bottom of the order, determining the adjustments needed to achieve an optimized amino acid profile. This accurate calculation is crucial in enhancing the overall protein quality, focusing on improving those amino acids that are typically less concentrated yet vital for certain functionalities. The precision of this approach not only ensures an efficient optimization process but also significantly increases the nutritional and therapeutic efficacy of the protein product.

Further, the disclosed embodiments provide a graphical representation as a visual indication that illustrates the improved and optimized amino acid profile of the protein sample alongside its profile before optimization. This graphical representation allows for a clear and immediate visualization of the enhancements in amino acid values. The comparative layout not only highlights the specific increases in lesser-valued amino acids but also underscores the overall enhancement of the protein's nutritional profile. This visual clarity facilitates easier interpretation and validation of the optimization process, facilitating better evaluation and decision-making for further developmental strategies.

Additionally, the disclosed embodiments utilize an efficient algorithm that quickly and accurately determines the value of the amino acids for the adjusted amino acid profile. This robust algorithm is designed to deliver precise results across a variety of protein samples, ensuring reliable outcomes in the optimization process. Its capability to quickly assess and modify amino acid values not only streamlines the enhancement procedure but also maintains high accuracy, making it a vital tool for improving protein formulations in diverse applications, from nutritional supplements to therapeutic products.

Referring now to the Figures, FIG. 1 illustrates an exemplary environment for a system 100 designed to implement a method for increasing muscle protein synthesis (MPS) relative to other nitrogenous processes. System 100 includes a combination of hardware and software. In some embodiments, the various methods described herein are implemented at least partially by hardware of one or more computing devices, such as one or more hardware processors executing instructions stored in one or more memories for performing various functions described herein. For example, descriptions of various components (or modules) as described in this application may be interpreted by one of skill in the art as providing pseudocode, an informal high-level description of one or more computer structures. The descriptions of the components may be converted into software code, including code executable by an electronic processor. System 100 illustrates only one of many possible arrangements of components configured to perform the functionality described herein. Other arrangements may include fewer or different components, and the division of work between the components may vary depending on the arrangement.

The depicted system comprises a first user 115 and a second user 118, who interact with the system through various devices connected to a network 106. In the context of the disclosed embodiments, the first user is identified as the manufacturer or seller of the protein product. This user is primarily responsible for the creation, optimization, and distribution of protein supplements or food products. The second user is the consumer or purchaser of the protein product. This user benefits directly from the optimized protein formulations, experiencing improved nutritional outcomes as a result of consuming products. Network 106 may include one or more packet switched networks, such as the Internet, or any local area networks, wide area networks, enterprise private networks, cellular networks, phone networks, mobile communications networks, or any combination thereof. Network 106 communicatively couples each component of system 100 and may utilize known security precautions such as encryption, passwords, limited Wi-Fi range, and the like.

The first user 115 utilizes first user device, such as a mobile device 112 or a laptop 114, and the second user 118 employs second user devices including a laptop 120 to access the system. The first user device, such as the laptop 114, in one example, belongs to a manufacturer or a seller of a product that may include protein sample or a protein powder, and the second user belongs to a buyer of the product. In other examples, the product may include cow's milk, peanuts, whey protein derived from milk, casein protein also from milk, soy protein, pea protein, another plant-based option rich in branched-chain amino acids and hypoallergenic, hemp protein that provides fiber and essential fatty acids and mixed plant proteins, which blend sources like pea, rice, hemp, and quinoa to offer a balanced amino acid profile and enhanced nutritional value.

The first and second users input specific data related to the protein products they are manufacturing, selling or consuming, utilizing a dynamically generated user interface on their device 112. Generally speaking, the first user device and the second user device are one or more of remote computing devices, such as a tablet computer, a smartphone, and a laptop computer. The mobile device 112 may encompass a variety of handheld or portable gadgets such as smartphones, tablets, or PDAs that offer flexibility and mobility for accessing the system in various contexts, such as in-field or remote environments. The laptop 114 represents a personal computer designed for portability and capable of handling more complex computational tasks. These devices are equipped with software and hardware that enable the user to obtain, process, and send data back to the server for further analysis. The devices may further include non-remote computing devices such as desktop computers and servers. Central to the system is a server environment 108, which houses a server 102 and a database 104. The server 102 and database 104 are interconnected and provide the computational and data storage capabilities necessary to execute the method. The server 102 is typically a powerful computer or cluster of computers designed to manage network resources and handle heavy processing tasks. Server 102 may be in communication with database 104. The database may store a variety of data, including data associated with any of the aforementioned communications. The database may permanently, or transiently store all or portion(s) of the data included in the aforementioned communications. In one embodiment, database 104 may be a relational database comprising a Structured Query Language (SQL) database stored in a SQL server, and may be distributed over one or more nodes or locations that are connected via network 106. Database 104 may accumulate data from the transactions that occur on system 100. The data from the transactions may be used, for instance, to train machine learned algorithms. For instance, machine learned algorithms for authenticating data may be produced from accumulated data.

Such exemplary communications described above may be sent via an appropriate protocol, such as via Hyper Text Transfer Protocol ("HTTP") and/or Hypertext Transfer Protocol Secure ("HTTPS"). Other transfer protocols may be used and are within the spirit and scope of the invention.

The described system and method improves muscle protein synthesis (MPS) relative to other nitrogenous processes by employing a sophisticated computational approach. In the context of nitrogenous processes within a protein sample, amino acids play multifaceted roles. Beyond their collective contribution to protein synthesis, individual amino acids exhibit distinct functions when isolated. Consider glycine, an essential amino acid. When a user faces starvation and consumes glycine powder, remarkable protective effects ensue. Specifically, the glycine powder acts as a safeguard against muscle wasting, preserving lean tissue even in the dire conditions of malnutrition. Furthermore, its benefits extend beyond muscle preservation and shields the user's entire body from harmful consequences of prolonged starvation. The second user device obtains an amino acid profile for a protein sample, which includes various amino acids listed by their respective gram values in descending order. This profile is then stored in the connected database 104. The process advances by executing a program on the server, which is part of a communications network. This program accesses the amino acid profile and follows instructions stored within the database to generate an adjusted amino acid profile for the protein product. The details of the working of the system and each component to execute the method and generating the adjusted amino acid profile are discussed in more detail in the subsequent figure descriptions.

Figure 1A:
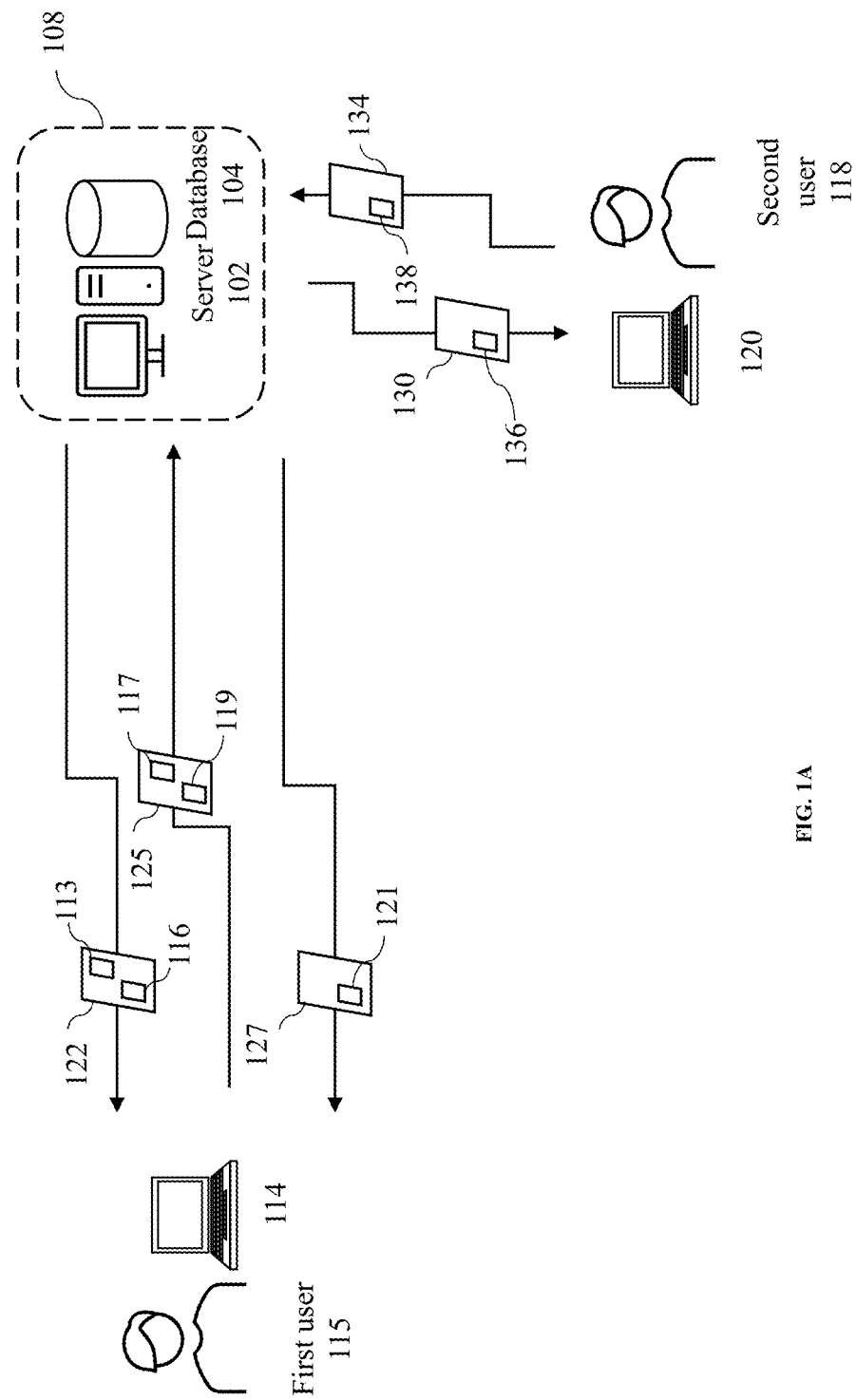
FIG. 1A is a schematic illustrating the flow of data in relation to example embodiments for increasing muscle protein synthesis (MPS) for protein samples by a server, according to an example embodiment.
Figure 2:
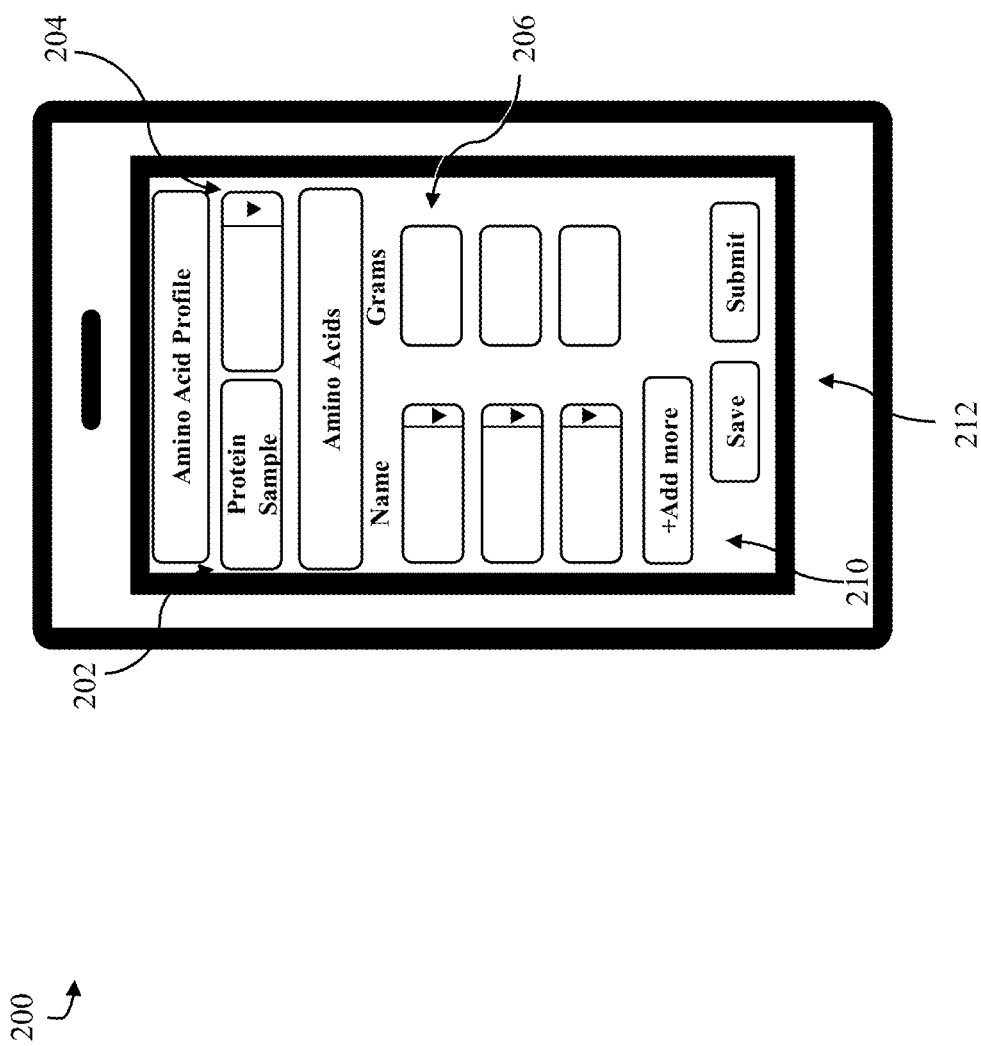
FIG. 2 is an example embodiment of a graphical user interface of a first user device, according to an example embodiment.
Figure 3A:
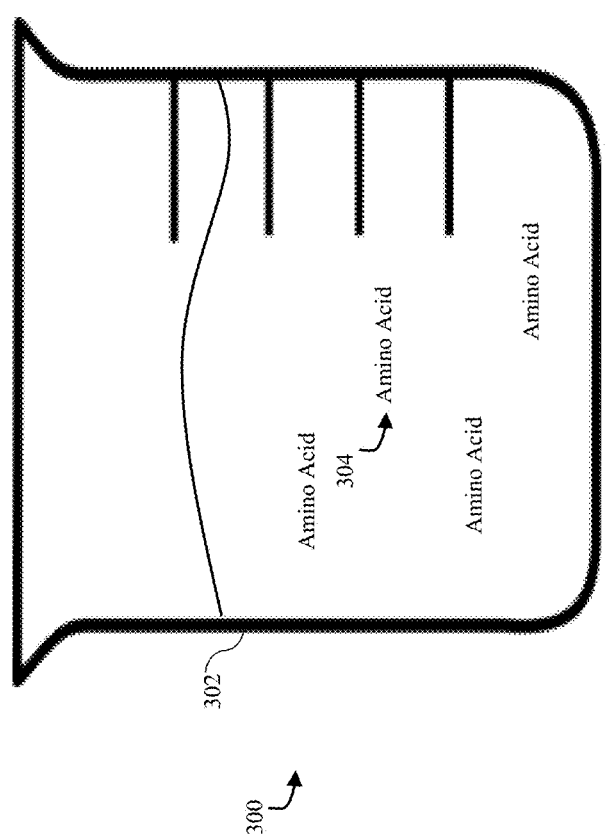
FIG. 3A illustrates a schematic illustrating a protein sample, according to an example embodiment.
Figure 3B:
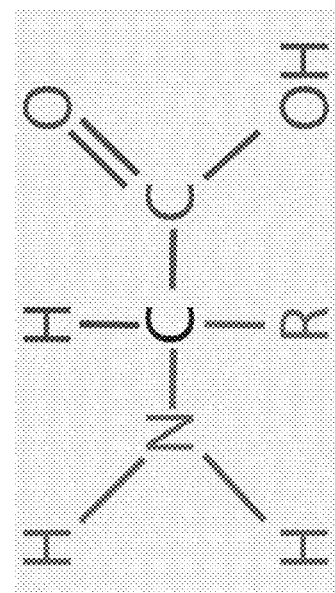
FIG. 3B illustrates a schematic illustrating a molecular structure of an amino acid of a protein sample.

With reference to FIGS. 1A, 2, 2A, 2B, 3A, 4A and 4B, various communications may be sent to and from the entities shown in system 100 using server 102. For instance, and with reference to the figures now including FIG. 1A, the server 102 may send an interface message 122, where the operator interface message 122 comprises an operator interface or graphical user interface related data 113 and 116. The data 113 and 116 may include graphical interface data for displaying a graphical user interface including layout information, images, styles, and commands that provide the appearance and functionality of the user interface. The interface message may be configured to display an interface configured to receive input, at the direction of the first user, which may include a graphical window with tabs to receive input from the first user. Additionally, the interface may include alpha numeric characters, audio content, and visual content, among others. FIG. 2 depicts a first user device having a GUI 200, which is a mobile device displaying a graphical user interface (GUI) designed to receive and process inputs related to a protein sample. For example, a protein sample as shown in FIG. 3A having amino acids shown in FIG. 3B. The interface displays a window for receiving inputs regarding an amino acid profile. On left portion of the screen, in section 202 of the interface, a dropdown menu labeled "Protein Sample" allows the user to select a specific protein sample from a predefined list. This dropdown is designed to facilitate easy selection and ensure that the correct protein sample is being analyzed. The section 202 further includes a section labeled "Amino Acids," which contains input fields for specifying the types displayed as graphical element "Name" in the selected protein sample. On the right portion of the interface, the sections 204 and 206 comprise another column for "Grams." For entering weight or values of each amino acid of the protein sample. Each row within these columns allows the user to input the name of an amino acid and the corresponding amount in grams. The dropdown menus in the "Name" column provide a list of amino acids, while the text fields in the "Grams" column are intended for numerical input. To accommodate additional amino acids, the interface includes an "+Add more" graphical button 210, which, when pressed, dynamically adds more rows to the input section, allowing the user to input more amino acid data without limitations on the number of entries.

At the bottom of the interface, two action graphical buttons 212 labeled "Save" and "Submit" are displayed. The "Save" graphical button is intended to save the current state of the input data locally on the device, enabling the user to review or edit the information later. The "Submit" graphical button is designed to send the finalized data to a server for further processing, such as analysis or storage. The graphical user interface as described operates within the system to provide an efficient and user-friendly method for inputting detailed protein sample information, ensuring accuracy and completeness. The materials involved in this interface include standard GUI components like dropdown menus, text fields, and buttons, all implemented using software technologies such as HTML, CSS, and JavaScript.

Figure 4A:
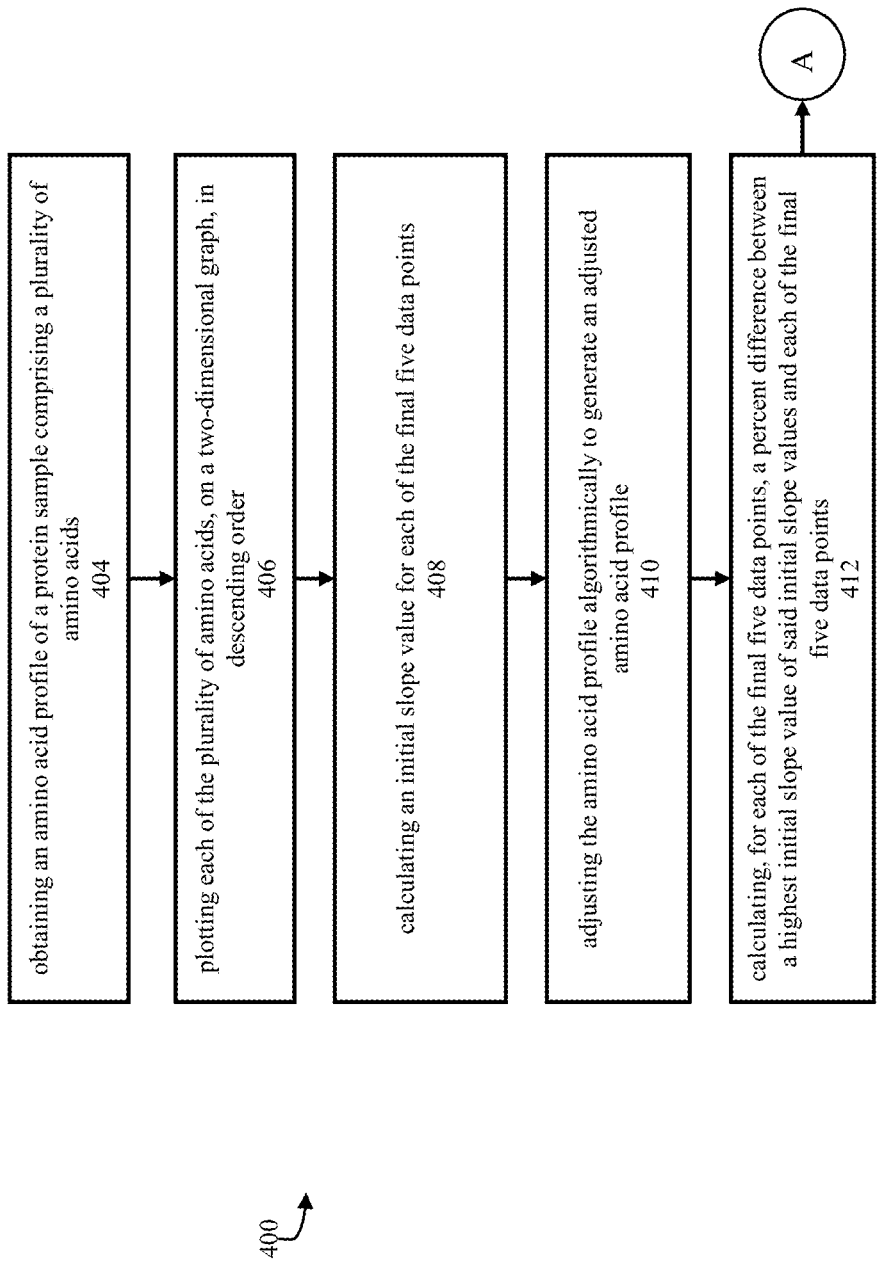
FIGS. 4A and 4B are flowchart diagrams illustrating the steps for a method for adjusting amino acid profile of a protein sample for increasing muscle protein synthesis (MPS), according to an example embodiment.
Figure 4B:
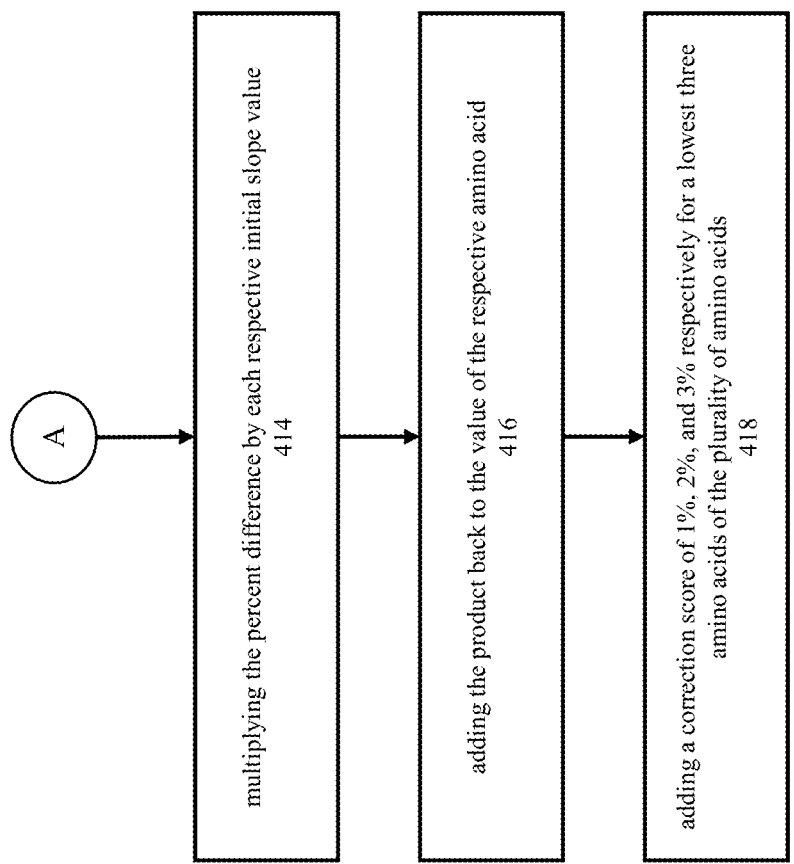

Referring to FIG. 1A, following the entry of the required data, the first user transmits a data packet 125 back to the server, which includes key data elements 117 and 119 pertinent to the protein sample or powder they are managing. The data elements 117 and 119 comprise the names and types of amino acids in the protein sample, and weight values of each amino acid, respectively. FIGS. 4A and 4B illustrate a flowchart of a method for analyzing and adjusting the amino acid profile of a protein sample. The process begins with obtaining an amino acid profile, as indicated in step 404. In this initial step, the amino acid profile of the protein sample is collected, encompassing a plurality of amino acids, each measured and recorded in terms of their specific values. This foundational data serves as the basis for subsequent analysis and adjustments. It is noted that the information regarding the amino acid profile is provided to the server by the first user, in other embodiments, the server may fetch the amino acid profile information from information and data available online.

Referring to FIG. 1A, in an alternative embodiment tailored to enhance user engagement and customization, the system extends its capabilities to incorporate a second user device, such as the laptop 120. This device is linked to a consumer or the second user 118 who may express interest in modifying the amino acid profile of the product. Addressing this need, the server dispatches an additional interface message 130 to the second user device having a data element 136 corresponding to interface elements, which activates the generation of a graphical user interface tailored to the consumer's specifications. The GUI on the second user device is similar to the GUI 200 of FIG. 2. Through this interface, the consumer meticulously inputs specific details, which are then encapsulated in a data message 134 sent back to the server containing data elements 138.

Upon reception of the aforementioned data from the first user device, the server initiates a sequence of processes wherein the data is methodically processed. This involves the generation of a data record, which is then accurately stored within a database 104. This may include a record ID, the details of the product such as name of the manufacturer of the product, phone, address. This database not only serves as a storage repository but also plays a critical role in managing the data for subsequent retrieval and processing, thereby supporting the system's core functionality. In accordance with the disclosed embodiments, the server plays a pivotal role in processing the data received from both the first and second users, who may be manufacturers, sellers, or consumers of a protein product. Upon receipt of the data, the server is tasked with generating an amino acid profile for the protein product. This profile is meticulously detailed, listing all constituent amino acids present in the protein product, as exemplified in FIG. 3C. Each amino acid is quantified, with values expressed per 100 grams of the product, providing a clear and measurable indication of the protein's composition. This amino acid profile is not merely generated for informational purposes but is integral to the creation of a comprehensive record for each protein product. The server stores this detailed profile within the record, ensuring that all relevant data concerning the protein's composition is maintained in an organized and retrievable format. This capability is crucial for ongoing quality control, regulatory compliance, and enhancement of product formulations.

Further enhancing the system's capabilities, the server is equipped with a specific algorithm saved within its system architecture. This algorithm is utilized to process the amino acid profile stored in the record, thereby generating an adjusted amino acid profile. The algorithm plots the amino acids on a two-dimensional graph, identifying the final five data points to establish a slope regression tail.

Figures 5A, 5B:
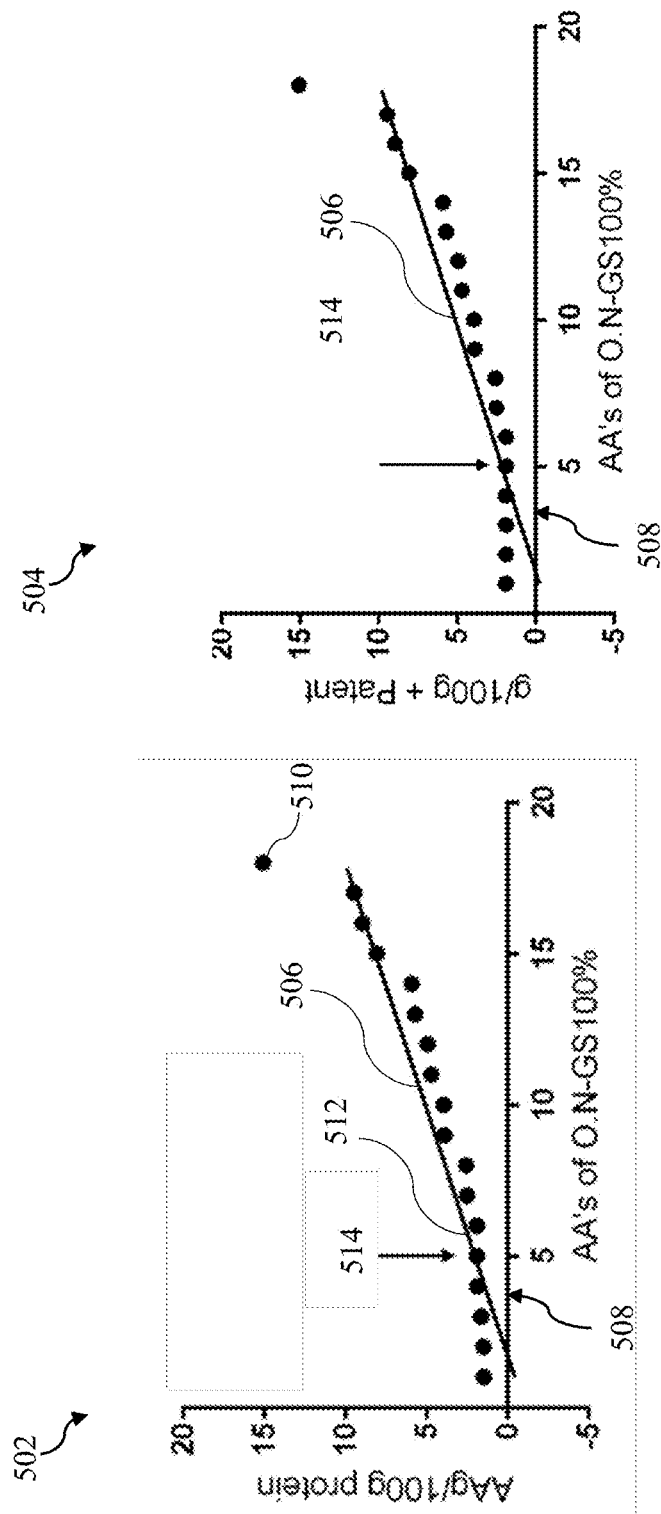
FIGS. 5A and 5B illustrate graphical representations of amino acids of a protein sample for an adjusted amino acid profile, according to an example embodiment.

Thereafter, the server may further process the data received. Referring to FIG. 4A, in step 406, the obtained amino acids are plotted on a two-dimensional graph in descending order based on their respective values, as shown in FIGS. 5A, 5C, 5E. This graphical representation allows for a clear visualization of the distribution and relative abundance of each amino acid within the protein sample. By arranging the amino acids in descending order, it becomes easier to identify patterns and trends that are critical for further analysis. Referring to FIG. 1A, the after plotting on the two-dimensional graph, the server transmits the graphical representation via the message 127 to the first user device for displaying the graph on the user device. The message 127 comprises a data element 121 corresponding to the values of x-axis and y-axis and corresponding amino acids of the protein sample. FIG. 2A illustrates the graphical representation displayed on the user device based on the amino acid of the protein sample. FIG. 2A illustrates a graphical user interface (GUI) 222 displayed on the user device, which visualizes the two-dimensional graph 224 corresponding to the amino acid profile of a protein sample. The GUI includes several interactive elements such as a section labeled "Amino Acid Profile," which displays the profile of amino acids present in the selected protein sample. Another section, "Protein Sample," allows users to select the type of protein sample being analyzed, with "Peanuts" chosen in this instance. Additionally, there is an "Initial Slope Value" section 230 that likely provides the initial slope value derived from the displayed graph. The graph itself features a Y-axis labeled "AA g/100 g protein," indicating the concentration of amino acids per 100 grams of protein. The X-axis is labeled "AA's of Peanuts," representing the various amino acids found in peanuts. Data points are plotted as dots along the graph, with a trendline illustrating the general trend of these data points. Error bars are included to show the variability or error in the data points. This GUI allows users to analyze and interpret the amino acid composition of selected protein samples, with specific emphasis on peanuts in this example.

In addition to sending the graphical representation to the user device, the server may further processes the data. Further processing of the data by the server is depicted in step 408 of FIG. 4A, where an initial slope value is calculated for each of the final five data points on the graph. This calculation uses the formula $M=(Y2-Y1)/(X2-X1)$, where Y represents the values of the amino acids and X represents their positions in the descending order. The slope values provide insights into the rate of change in amino acid values across the final data points, which is essential for understanding the dynamics of the amino acid distribution. Step 410 involves adjusting the amino acid profile algorithmically to generate an adjusted amino acid profile. The algorithm considers the initial slope values and other relevant factors to refine the profile. This step aims to optimize the amino acid composition for specific criteria, such as enhancing nutritional value or improving functional properties. The use of an algorithm ensures that the adjustments are precise and based on rigorous computational analysis.

In step 412, the algorithm calculates the percent difference for each of the final five data points. This involves comparing the highest initial slope value with each of the final five data points' slope values. The percent differences highlight deviations and variations among the data points, which are crucial for fine-tuning the adjusted amino acid profile. This step ensures that the final profile meets the desired specifications and standards. Further, the method includes multiplying the percent difference by each respective initial slope value, as indicated in step 414. This step is critical as it refines the adjustments based on the variations identified in the initial slope values. By multiplying the percent difference by the initial slope value, the process generates a product that reflects the adjusted value for each of the final five data points, ensuring precise modifications to the amino acid profile. Following this, step 416 involves adding the product back to the original value of the respective amino acid. This addition incorporates the adjustments into the amino acid profile, effectively refining the overall composition. The adjusted values represent a more accurate and optimized profile for the protein sample, which is crucial for achieving the desired nutritional and functional characteristics.

In the step 418, introduces a correction score for the lowest three amino acids in the profile. Specifically, a correction score of 1%, 2%, and 3% is added respectively to these amino acids. This step ensures that even the amino acids present in lower concentrations are adequately adjusted, contributing to a more balanced and comprehensive amino acid profile. The application of these correction scores further fine-tunes the profile, making it more robust and tailored to specific requirements. Each of these points has an initial slope value calculated using a specific formula. Subsequent algorithmic adjustments refine the amino acid profile based on the percent difference between the highest slope value and each of the final five data points, adjusting their weights accordingly. The lowest three amino acids in the slope regression tail receive an incremental correction score of 1%, 2%, and 3%, respectively. This computational method enhances the accuracy and effectiveness of the amino acid profile, potentially optimizing the protein's capacity for muscle protein synthesis, thereby presenting a substantial improvement over existing methods by tailoring protein profiles more closely to biological needs. Collectively, the steps outlined in FIGS. 4A and 4B enhance the precision and effectiveness of the amino acid profile adjustment process. By systematically applying calculated corrections and adjustments, the method ensures that the resulting amino acid profile is finely tuned to meet specific nutritional and functional criteria. This comprehensive approach is essential for developing high-quality protein products with optimized amino acid compositions, ultimately improving their applicability in various health, nutrition, and biotechnological applications.

The adjustments made by this algorithm are based on predefined criteria aimed at optimizing the nutritional value of the protein, enhancing its functional properties in food products, or tailoring the amino acid balance to meet specific dietary needs or consumer preferences. The ability to dynamically generate and adjust amino acid profiles based on algorithm-driven insights positions this system as a significant improvement over prior art. It provides a dynamic, responsive approach to protein product management, facilitating enhanced product development and optimization that can directly influence market competitiveness and consumer satisfaction. This system, therefore, not only supports the operational needs of protein manufacturers and sellers but also serves as a critical tool in advancing the science of protein engineering and nutrition. In another example, after adjusting the amino acid profile, the server generates another graphical representation of the adjusted amino acid profiles, shown in FIGS. 5B, 5D, 5E on the two dimensional graph and transmits a message to the first user device for displaying a GUI showing the graph. FIG. 2B depicts a graphical user interface (GUI) 227 on a user device, showcasing a two dimensional graph 226 that corresponds to the adjusted amino acid profile of a protein sample. The GUI displays the amino acid profile, of the protein sample which is peanuts. The second element is labeled "Adjusted Slope Value," indicating a recalibrated slope value 232 derived from the displayed amino acid data corresponding to the adjusted amino acid profile. The two dimensional graph features a Y-axis labeled "g/100 g+Peanut," signifying the quantity of amino acids per 100 grams of protein, adjusted for peanuts. The X-axis is labeled "Peanuts AAs," representing the specific amino acids found in peanuts. Data points are plotted as dots along the graph, with a trendline showing the overall trend of these data points. Error bars are included to reflect variability or error in the data measurements. This GUI is designed to allow users to easily and analyze and interpret the amino acid composition of the protein sample with a specific focus on peanuts, facilitating a deeper understanding of the protein's characteristics and variability.

Figure 2C:
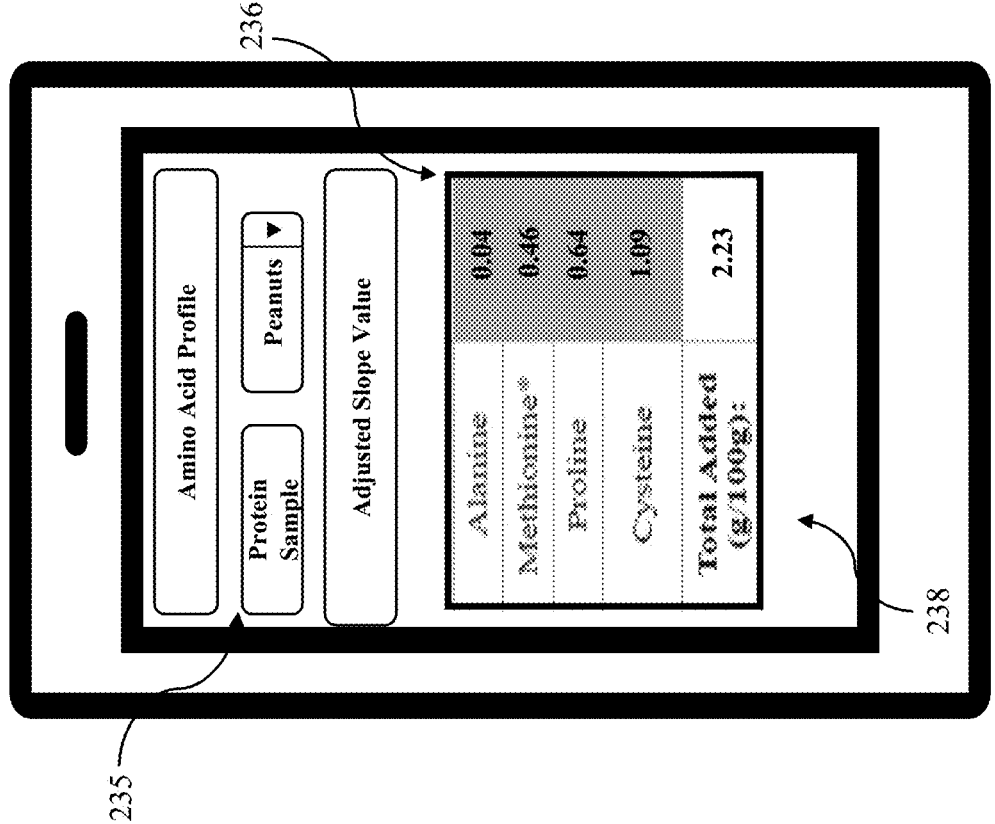

In another embodiment, after the calculation is performed by the server using the algorithm, the algorithm outputs the amino acids and their values to be added to the protein sample, and sends a display message to the first user device to be displayed on the GUI 235. FIG. 2C illustrates the graphical user interface (GUI) 235 displayed on a first user device. This GUI features several interactive elements designed to facilitate the user's interaction with amino acid profile data. The GUI displays a table 236, which shows the different values of the amino acids to be added based on the algorithmic calculation. The table lists the amino acids along with their respective values that are based on differences between the values in the original amino acid profile and the adjusted amino acid profile, which are as follows: Alanine at 0.04, Methionine* at 0.46, Proline at 0.64, and Cysteine at 1.09. Additionally, the table includes the "Total Added (g/100 g)," 238 which aggregates the values of the amino acids to a total of 2.23 grams (approx.).

Figure 6A:
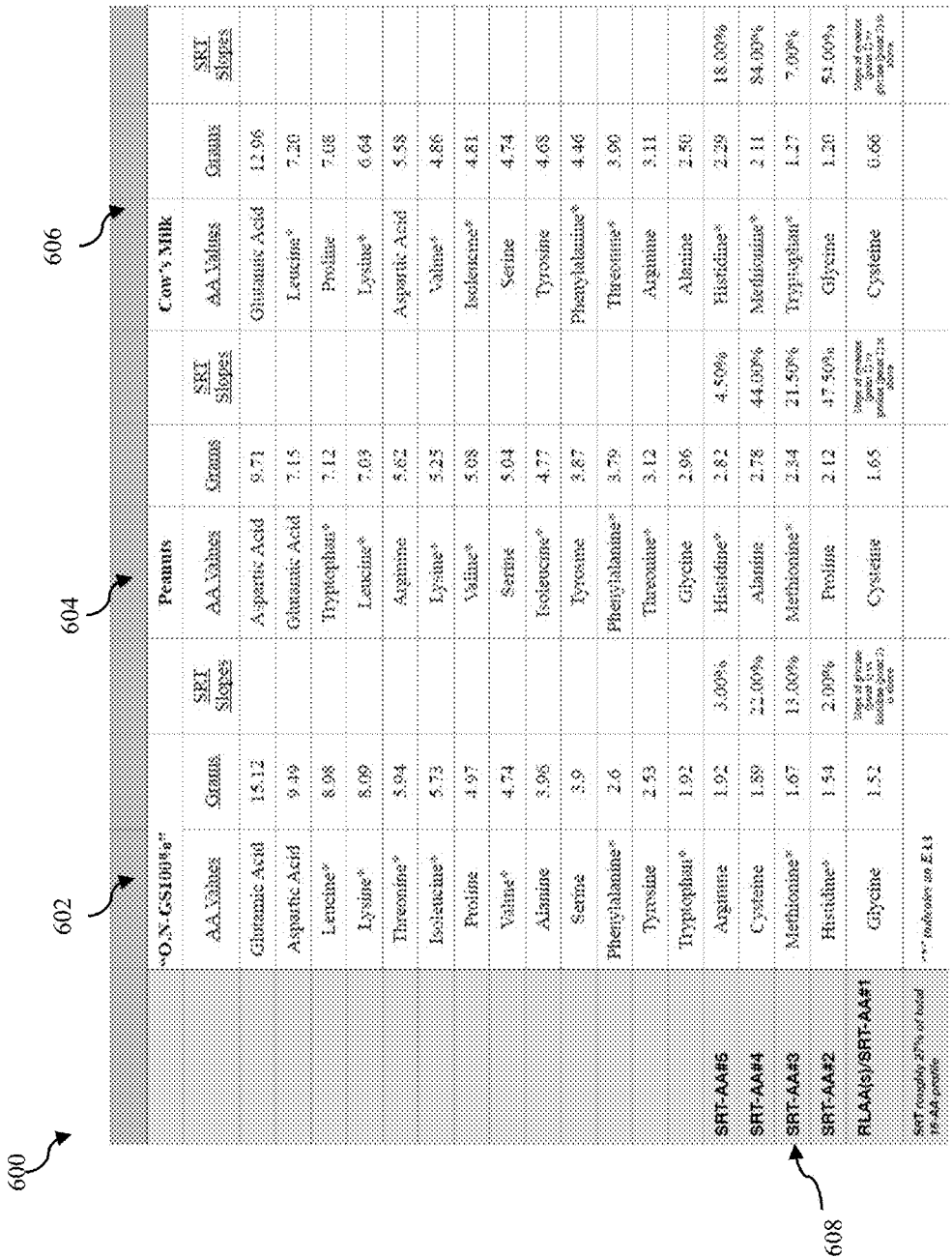

The process of determining the total added value is based on determining the difference between the amino acid values of FIGS. 6A and 6B and aggregating the differences. For example, the adjusted amino acid profile for Alanine in peanuts is noted at 2.82 grams in FIG. 6B as opposed to the 2.78 grams in the unmodified profile of FIG. 6A, reflecting a net increase of 0.04 grams. The concentration of Methionine increases from 2.34 to 2.80 grams, providing a differential of 0.46 grams. In other amino acids, increments are observed with Proline from 2.12 to 2.76 and Cysteine from 1.65 to 2.74, where the increases are recorded at 0.64 and 1.09 grams, respectively, summing to the total enhanced weight of 2.23 grams. In light of the updated information regarding the values of amino acids to be added, as depicted on the user device, users and/or manufacturers are provided with direct and precise information concerning the specific weights of these amino acids required to be added to the protein sample. This essential data facilitates the optimization of the amino acid profile of the protein sample, ensuring that the composition is tailored to achieve enhanced nutritional value and functionality. The graphical user interface (GUI), such as GUI 235 displayed on the first user device, clearly enumerates the adjusted quantities of each amino acid, for instance, Alanine, Methionine, Proline, and Cysteine, as calculated by the proprietary algorithm. Furthermore, the GUI displays the cumulative weight of the amino acids added per 100 grams of the protein sample, thereby allowing users or manufacturers to precisely calibrate the additions according to the algorithm's recommendations. This interface and the data it presents serve as a crucial tool in the manufacturing process, enabling the systematic adjustment of amino acid levels to meet specific dietary requirements or performance criteria, ultimately improving the quality and effectiveness of the protein products.

FIG. 3A depicts a protein sample 300, such as a cow's milk, housed within a container 302. The figure shows the dispersal of several amino acids 304, within the confines of the container. The visual representation is critical for understanding the composition of the protein sample, as it identifies the presence of amino acids, which are the fundamental building blocks of proteins. These amino acids are essential for various biological functions and contribute significantly to the nutritional value of the protein sample. In detail, FIG. 3B further elucidates the molecular structure 310 of these amino acids. The figure shows a general amino acid structure, central to understanding protein chemistry. The structure includes a central carbon atom, an amino group (NH2), a carboxyl group (COOH), a hydrogen atom (H), and a variable side chain or R-group. The R-group is crucial as it varies between amino acids, imparting unique chemical properties and functions to each. This diagram serves not only as an educational tool about amino acid structure but also as a foundation for discussing how amino acids contribute to the functionality and nutritional value of the protein sample shown in FIG. 3A.

FIG. 3C presents a comprehensive amino acid profile 340 amino acids 342 for three types of protein, whey 344, casein 346, and soy 348, with values expressed per 100 grams of the product. This figure highlights the presence and quantity of various amino acids in each protein type, providing valuable insight into their nutritional composition. Whey protein demonstrates a high content of essential amino acids, particularly leucine, which is crucial for muscle protein synthesis. It also contains significant amounts of glutamic acid and aspartic acid, which play vital roles in metabolic processes and energy production. Other notable amino acids in whey include lysine and isoleucine, which are essential for growth and tissue repair.

Casein protein, on the other hand, is rich in glutamic acid and proline, contributing to its unique slow-digesting properties. This makes casein an excellent choice for sustained amino acid release. It also contains higher levels of histidine and methionine compared to whey, supporting various physiological functions, including enzyme activity and antioxidant defense. Soy protein stands out for its high arginine content, which supports cardiovascular health and enhances nitric oxide production. It also contains a balanced profile of essential amino acids, making it a complete plant-based protein source. The presence of phenylalanine and tyrosine in soy protein aids in neurotransmitter synthesis, which is crucial for brain function.

The superscripts in FIG. 3C indicate essential amino acids (denoted by "a") and branched-chain amino acids (denoted by "b"). Essential amino acids, such as histidine, lysine, and threonine, are vital as they cannot be synthesized by the body and must be obtained through diet. Branched-chain amino acids, including isoleucine, leucine, and valine, are particularly important for muscle recovery and growth. Overall, FIG. 3C provides a detailed comparison of the amino acid compositions of whey, casein, and soy proteins, underlining their respective benefits and applications in nutrition and health. This information is essential for developing dietary supplements, functional foods, and specialized nutrition products tailored to meet specific dietary needs and health goals.

Figure 4C:
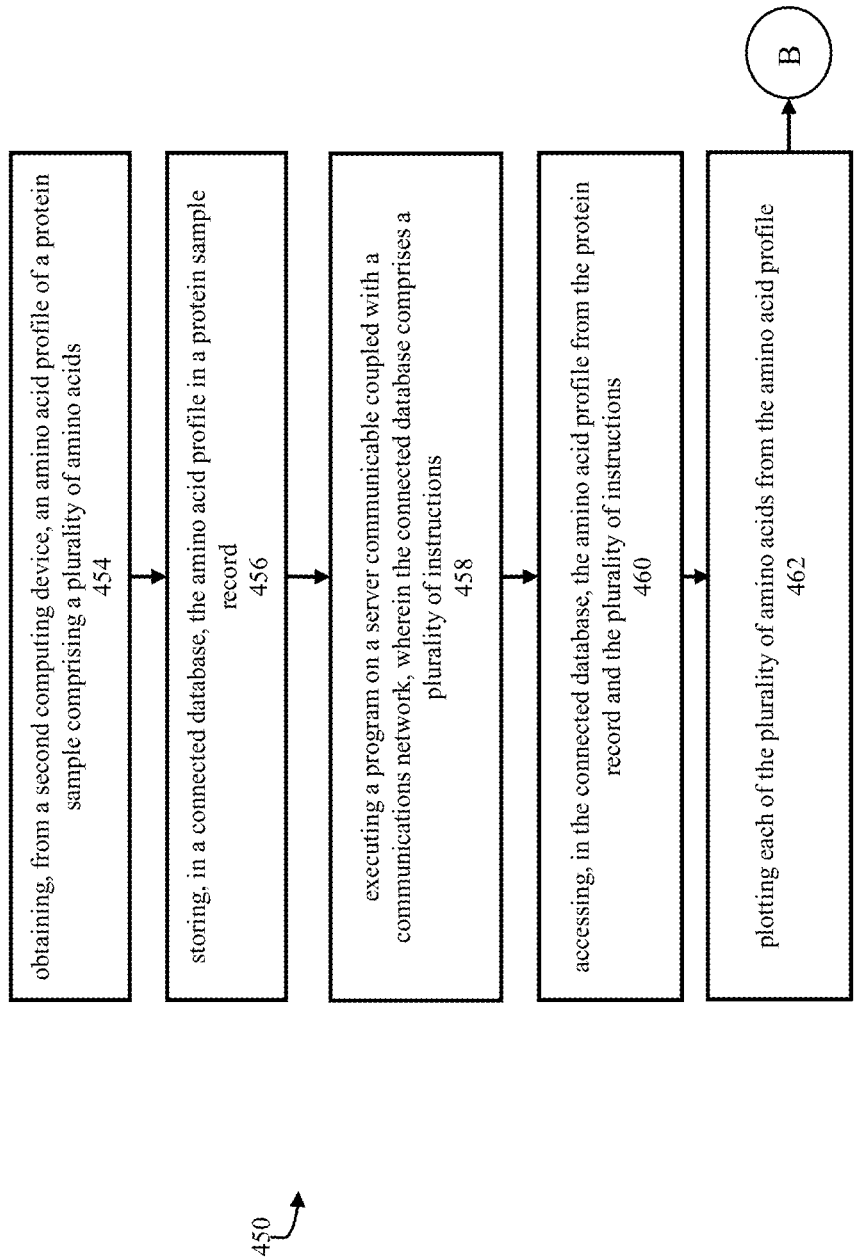
FIGS. 4C, 4D, and 4E illustrates a flow diagram of a method for adjusting amino acid profile of a protein sample according to another example embodiment.
Figure 4D:
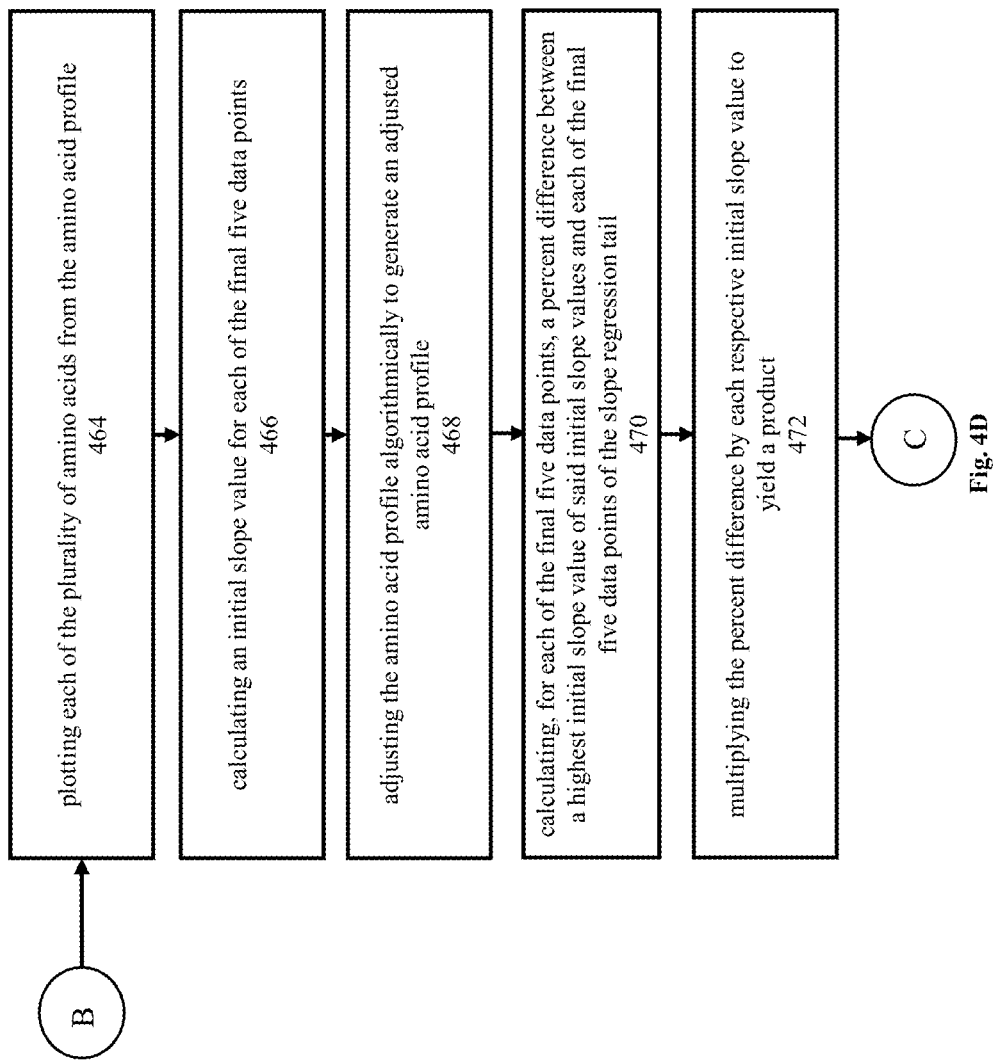
Figure 4E:
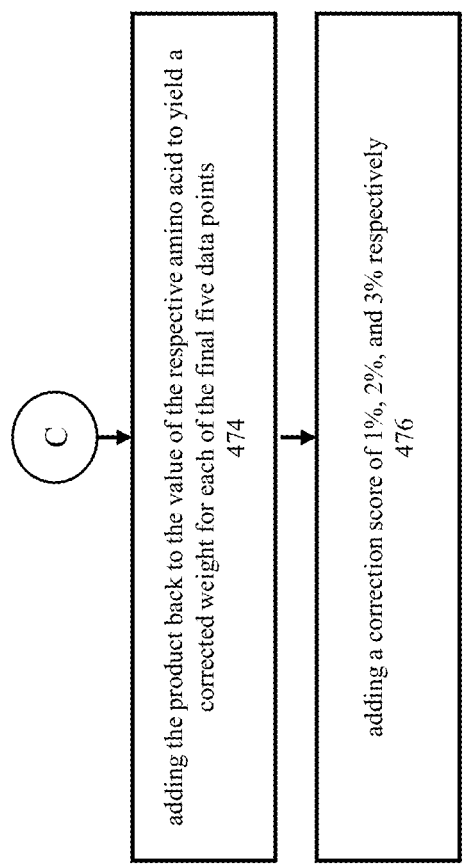

FIG. 4C, FIG. 4D, and FIG. 4E depict a method flow for adjustment and optimization of the amino acid profile to meet specific criteria. In FIG. 4C, the process begins with obtaining an amino acid profile of a protein sample from a second computing device, as indicated in step 454. This profile includes a plurality of amino acids, each quantified and recorded. Once the profile is obtained, it is stored in a connected database, creating a protein sample record as shown in step 456. This record is crucial for maintaining the integrity and accessibility of the profile for further processing. Following storage, a program is executed on a server that is communicably coupled with a communications network, as described in step 458. This server accesses the connected database, which contains a plurality of instructions necessary for processing the amino acid profile. In step 460, the server retrieves the amino acid profile from the protein record along with the relevant instructions. Subsequently, in step 462, each amino acid from the profile is plotted on a two-dimensional graph. This graphical representation helps visualize the distribution and relative abundance of amino acids within the protein sample.

The method flow diagram depicted in FIG. 4D continues the process of analyzing and adjusting the amino acid profile of a protein sample, building upon the steps detailed in the preceding figures. This portion of the method begins with step 464, wherein each of the plurality of amino acids from the previously obtained amino acid profile is plotted on a two-dimensional graph. This graphical representation, arranged in descending order based on the amino acid values, facilitates the visualization of the distribution and relative abundance of each amino acid within the protein sample. Subsequently, in step 466, the process involves calculating an initial slope value for each of the final five data points on the graph. This calculation employs the formula $M=(Y2-Y1)/(X2-X1)$, where Y represents the values of the amino acids and X denotes their positions in the descending order. The initial slope values provide critical insights into the rate of change in amino acid concentrations across the final data points, forming the basis for further adjustments.

Following the calculation of the initial slope values, step 468 entails adjusting the amino acid profile algorithmically to generate an adjusted profile. This adjustment is performed using a predefined algorithm that takes into account the initial slope values and other relevant factors. The objective of this step is to optimize the amino acid composition, enhancing the nutritional and functional properties of the protein sample to meet specific criteria. In step 470, the process calculates the percent difference for each of the final five data points by comparing the highest initial slope value with each respective slope value of the final five data points in the slope regression tail. This calculation is crucial for identifying deviations and understanding the variability among the data points, which are necessary for precise adjustments. The final step depicted in FIG. 4D is step 472, where the percent difference calculated in the previous step is multiplied by each respective initial slope value to yield a product. This product reflects the adjusted value for each of the final five data points, ensuring that the corrections made are systematically applied to the amino acid profile. By incorporating these adjustments, the method refines the amino acid profile, making it more accurate and aligned with the desired specifications.

The method flow diagram depicted in FIG. 4E illustrates the final steps in the process of adjusting the amino acid profile of a protein sample. This part of the method continues from the preceding steps detailed in FIG. 4D and finalizes the adjustments to achieve the desired profile. In step 474, the process involves adding the product, which was calculated by multiplying the percent difference by each respective initial slope value, back to the original value of the respective amino acid. This addition yields a corrected weight for each of the final five data points. By incorporating the calculated product into the amino acid values, the method ensures that the adjustments are precisely applied, resulting in a more accurate and optimized amino acid profile. Following the incorporation of the corrected weights, step 476 applies an additional correction score to further refine the profile. Specifically, a correction score of 1%, 2%, and 3% is added respectively to the lowest three amino acids in the profile. This step ensures that even the amino acids present in the smallest quantities are appropriately adjusted, contributing to a balanced and comprehensive amino acid profile. The application of these correction scores enhances the overall accuracy and optimization of the protein sample, aligning it with specific nutritional and functional criteria. Overall, the steps outlined in FIG. 4E are critical for finalizing the adjustments to the amino acid profile. By systematically incorporating the calculated corrections and applying additional adjustment scores, the method ensures that the resulting amino acid profile is finely tuned to meet specific requirements. This detailed approach is essential for developing high-quality protein products with optimized amino acid compositions, which are valuable for applications in health and nutrition.

In another embodiment, the method for increasing muscle protein synthesis (MPS) relative to another nitrogenous process comprises obtaining, from a second computing device, an amino acid profile of a protein sample comprising a plurality of amino acids, wherein each of the plurality of amino acids comprise a value measured in grams and wherein the value of the plurality of amino acids are sorted from greatest to least, storing, in a connected database, the amino acid profile in a protein record, and executing a program on a server communicable coupled with a communications network. The connected database comprises a plurality of instructions for accessing the amino acid profile from the amino acid record and the plurality of instructions in the connected database, and identifying from the amino acid profile a subset of five target amino acids comprising five lowest values of the amino acid profile. Further, the instructions are for calculating an initial slope value for each of the subset of five target amino acids, wherein the initial slope value is defined as $M=(Y2-Y1)/(X2-X1)$, with Y representing each value for each of five target amino acids and X representing a position, in a descending order for each of the target amino acid, and adjusting the amino acid profile algorithmically to generate an adjusted amino acid profile.

In various embodiments, the amino acid profile is adjusted by calculating, for each of the target amino acids, a percent difference between (i) a highest initial slope value of said initial slope values and (ii) the initial slope values of each target amino acids of the plurality of amino acids, and multiplying, for each of the target amino acids, the percent difference by each respective initial slope value to yield a product. Further, the amino acid profile is adjusted based on adding, for each of the target amino acids, the product back to the value of the respective target amino acid to yield a corrected weight for each of target amino acids. For a lowest three of the target amino acids, adding a correction score of 1%, 2%, and 3% respectively, by multiplying the corrected weight for each of the lowest three of the target amino acids by the correction score and then subtracting that correction value from the corrected weight, and providing, to the second computing device a message to display (i) a graphical representation displaying on a two dimensional graph the initial slope value for the target amino acids that define a slope regression tail and (ii) a second graphical representation displaying the two dimensional graph an adjusted slope value for an adjusted target amino acids for the adjusted amino acid profile that define an adjusted slope regression tail.

In an example embodiment, with reference to FIGS. 6A and 6B, the disclosed algorithm for determining amino acid (AA)-profile specific alterations comprises a series of computational steps, exemplified for the protein sample denoted as "O.N-GS100%". The output of the algorithm results in the adjustment of SRT-AA #4 (Methionine) quantities, measured in grams. Initially, in the first step the calculation of the percent difference between the values of SRT-AA #5 (Arginine) of and SRT-AA #2 (Histidine) of amino acid profile of FIG. 6A is performed. This is achieved by subtracting the value of SRT-AA #2 (1.54 grams) from the value of SRT-AA #5 (1.92 grams), yielding a difference of 0.38 grams. This difference is then divided by the value of SRT-AA #2 (1.54 grams), resulting in a quotient of 0.25 (Product #1). Subsequently, in the next step, the quotient obtained from Step 1 (Product #1) is multiplied by the value of SRT-AA #2 (1.54 grams), producing a result of 0.39 grams (Product #2). In the next step, the value derived in Step 2 (Product #2) is added to the original value of SRT-AA #4 (1.54 grams), resulting in a corrected weight of 1.93 grams (Product #3). In the subsequent step, a correction factor ranging from 1% to 3% is applied to the value of SRT-AA #3-1. For a 2% correction, the value obtained in Step 3 (1.93 grams) is multiplied by 0.02, resulting in a correction factor of 0.04 grams. This correction factor is then subtracted from the value obtained in Step 3, yielding a final adjusted weight of 1.89 grams. The alteration in the values of the SRT values, specifically the SRT-AA #2 (Histidine), is depicted in FIGS. 6A and 6B. FIG. 6A illustrates the previous value of SRT-AA #2 (Histidine), whereas FIG. 6B displays the updated value of SRT-AA #2 (Histidine) as 1.89 grams. Further, FIGS. 5A-5F provide graphical representations of the updated SRT values of the amino acids compared to their previous values across various protein samples. These figures illustrate a change in the slope for the updated SRT values for each protein sample, effectively demonstrating the algorithm's ability to modify and optimize the amino acid profiles according to specific requirements and variations in each sample. For exemplary purposes, the disclosed calculation is demonstrated using only one protein sample. It should be understood that in various embodiments, the algorithm is designed to perform this analysis across each of the specified SRT values for each protein sample. This systematic application of the algorithm ensures the determination and updating of the SRT values for the amino acids for each protein sample, thereby facilitating precise adjustments tailored to the specific needs of each sample.

FIG. 5A illustrates the plot 502 for the original amino acid profile of a protein sample. In this figure, the x-axis is labeled "AA's of O.N-GS100%" 508, representing the types of amino acids present in the protein sample. The y-axis measures the amino acid concentration in grams per 100 grams of protein (AAg/100 g protein), facilitating an accurate depiction of the protein's composition. The plot contains multiple data points 510, each marking the concentration of individual amino acids in the protein sample. A trend line 506 is introduced to visualize the overall distribution and concentration trends of the amino acids. Notably, the plot includes a slope regression tail (SRT) 512, depicted at the end of the amino acid sequence, which indicates the slope of the final five data points. This metric is crucial as it provides insights into the rate of change in amino acid concentrations, highlighting significant variations at the end of the profile. An arrow 514 marks the initiation point of this SRT, emphasizing its role in the analysis. FIG. 5A portrays the original amino acid profile, where the trend line shows a steeper slope regression tail (SRT), indicating greater variability in amino acid concentrations towards the end of the profile. This variability is significant as it suggests a less consistent protein composition, which can affect the protein's functional properties and its suitability for specific nutritional applications. The presence of a steeper SRT in the original amino acid profile highlights the concentration disparities among amino acids, particularly those appearing towards the sequence's end.

FIG. 5B presents the plot 504 for the amino acid profile post-algorithmic adjustments. Maintaining the same x-axis as FIG. 5A, this figure introduces a new y-axis measurement, now indicating the adjusted amino acid concentration (g/100 g), reflecting the algorithmic enhancements applied to the profile. Similar to FIG. 5A, multiple data points 510 represent the adjusted concentrations of each amino acid, with a trend line 506 illustrating the new distribution pattern. The adjusted plot's SRT 512 exhibits a more horizontal alignment compared to the steeper SRT in FIG. 5A. This alteration suggests a more stabilized and balanced distribution of amino acids, particularly noticeable at the tail end of the profile. An arrow 514 again points to where this more horizontal SRT begins, underscoring the improved uniformity and optimization of the amino acid distribution. In contrast to FIG. 5A, FIG. 5B displays the adjusted amino acid profile post-application of the algorithmic enhancements. The critical observation in this figure is the more horizontal orientation of the SRT, which denotes a marked improvement in the evenness and balance of the amino acid distribution. A more flat or horizontal SRT towards the end of the profile indicates that the final amino acids in the sequence have been adjusted to levels that are closer to those of their predecessors, resulting in a smoother transition and reduced concentration spikes. This uniformity is advantageous as it signifies a more stable and predictable profile, which is often critical for enhancing the protein's bioavailability and functionality.

The flattened SRT in FIG. 5B reflects the success of the algorithmic adjustments in normalizing the amino acid levels and reducing the extremes that might detract from the protein's overall quality. By achieving a more consistent distribution of amino acids, the protein sample becomes more tailored to meet specific dietary needs and more effective in applications where gradual amino acid release is beneficial, such as in sustained energy and muscle recovery products. Both FIG. 5A and FIG. 5B provide a visual representation of the amino acid profiles before and after the algorithmic adjustments. This visual comparison is crucial as it not only illustrates the quantitative changes in amino acid concentrations but also highlights the qualitative enhancements in the profile's structure. The plots effectively demonstrate how the disclosed embodiments of the algorithm optimize the protein's amino acid profile, making it more aligned with nutritional standards and functional requirements. In conclusion, the comparative analysis and visual representations in FIG. 5A and FIG. 5B are central to understanding the impact of the disclosed algorithmic adjustments. They clearly show how the adjustments lead to a more balanced and functionally advantageous amino acid profile. This optimized profile, as demonstrated by the more horizontal SRT in FIG. 5B, is a testament to the efficacy of the disclosed embodiments, providing significant improvements over traditional methods and offering a sophisticated approach to protein sample optimization. This enhanced method is not only beneficial for achieving desired nutritional outcomes but also for maintaining consistency and efficacy in protein-based products, underscoring the patent's applicability and value in the field of biotechnology and health sciences.

Figure 5D:
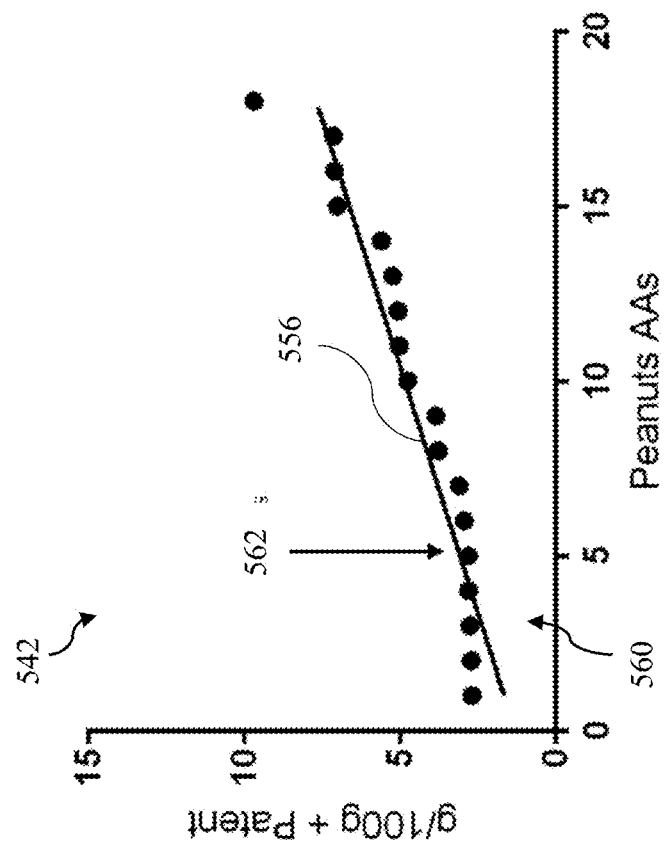
FIGS. 5C and 5D illustrate graphical representations of amino acids of another protein sample for an adjusted amino acid profile, according to an example embodiment.
Figure 5C:
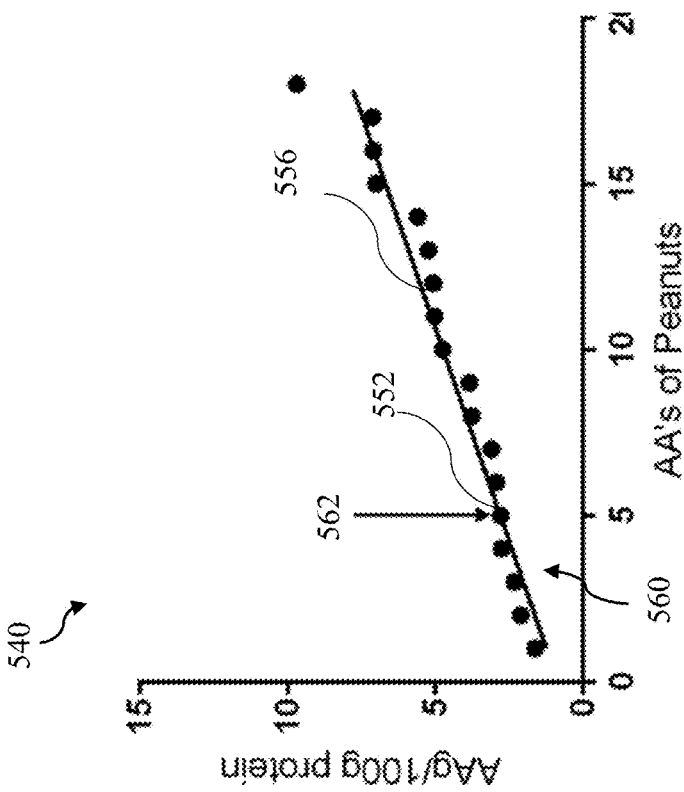

The illustrations in FIG. 5C and FIG. 5D further exemplify the refined approach to evaluating and optimizing the amino acid profiles in protein samples, specifically using peanuts as the sample under analysis. These figures collectively demonstrate the application and effectiveness of the patented method for optimizing amino acid distribution, critical for enhancing the nutritional profile of commonly consumed legumes such as peanuts. FIG. 5C provides a detailed graphical representation of the amino acid profile for a peanut protein sample prior to any adjustments. The x-axis, marked as "AA's of Peanuts" 560, lists the sequence of amino acids analyzed within the sample. The y-axis quantifies these amino acids, presenting their concentration in grams per 100 grams of protein (AAg/100 g protein) 540. This graph includes a series of data points 556, each pinpointing the concentration of a distinct amino acid within the sample. A trend line 552 is plotted to visualize the distribution and trends in amino acid concentrations across the sample. Notably, this figure includes an arrow 562 to indicate where the slope regression tail (SRT) begins, highlighting the segment of the amino acid sequence where significant variability or a change in concentration trend might occur.

FIG. 5D transitions from the raw amino acid profile to showcasing the effects of the patented algorithmic optimization on the same peanut protein sample. Maintaining the same x-axis configuration as FIG. 5C for comparative purposes, the y-axis in FIG. 5D is adjusted to represent the amino acid concentration post-optimization, noted as g/100 g 542. This figure also displays a series of data points 556, now reflecting the optimized concentrations of amino acids. The trend line 552 in this graph illustrates the altered distribution pattern post-adjustment, which ideally demonstrates a more uniform and optimized amino acid profile. The SRT in this figure is distinctly more horizontal as indicated by the arrow 562 in FIG. 5D, suggesting that the adjustments have resulted in a stabilization of the concentration variations towards the end of the amino acid sequence. The direct comparison between FIG. 5C and FIG. 5D underscores the transformation in the amino acid profile due to the patented algorithmic adjustments. In FIG. 5C, the initial profile may show a steeper SRT, indicating abrupt changes in concentration at certain points, which could potentially affect the protein's overall nutritional impact. Conversely, FIG. 5D illustrates a smoother, more horizontal SRT, signifying a balanced amino acid profile with reduced extremes in concentration variability. This adjustment not only enhances the predictability and uniformity of the amino acid levels but also optimizes the nutritional quality of the peanuts, making the protein more suitable for targeted dietary applications.

FIG. 5E and FIG. 5F, display optimizing amino acid profiles in cow's milk. These figures provide the efficacy of the method for enhancing the nutritional value of dairy products through precise amino acid adjustment. FIG. 5E presents a graphical representation of the original amino acid profile in cow's milk. The x-axis, labeled as "AA's of Cow's Milk" 580, lists the sequence of amino acids analyzed within the cow's milk sample. The y-axis, labeled as AAg/100 g protein 570, quantifies these amino acids in grams per 100 grams of protein, displaying a range of concentrations across different amino acids. The plot is populated with data points 575, each representing the concentration of a specific amino acid in the milk. A trend line 578 helps to illustrate the overall trend and distribution of amino acid concentrations within the sample. This line shows the initial state of amino acid levels before any algorithmic adjustment is applied.

FIG. 5F transitions from displaying the original amino acid concentrations to showing the effects of the patented adjustments. It maintains the same x-axis 580 for a consistent comparison, while the y-axis 572 now denotes the adjusted amino acid concentration labeled as g/100 g+Patent, indicating the enhancement following the patented method. The plot in this figure also features data points 575 which correspond to the adjusted concentrations of amino acids. The trend line 578 in FIG. 5F demonstrates a significant change in the distribution pattern of amino acids, becoming more uniform across the sequence. Notably, this figure highlights where the slope regression tail (SRT) begins, showing a marked stabilization in the concentration variability towards the end of the sequence. The juxtaposition of FIG. 5E and FIG. 5F provides a clear visual representation of the improvements in the amino acid profile of cow's milk due to the application of the disclosed method. FIG. 5E shows a more variable and possibly less optimal distribution of amino acids, as evidenced by the original trend line 578. In contrast, FIG. 5F exhibits a trend line 578 that is smoother and more horizontal, indicating a balanced and stabilized amino acid distribution post-adjustment. This comparative visualization underscores the effectiveness of the patented method in optimizing amino acid profiles, which is crucial for enhancing the nutritional quality of dairy products.

These figures collectively serve to demonstrate the practical application and benefits of the patented method in real-world food products. By adjusting the amino acid profiles in cow's milk, the method ensures enhanced bioavailability and nutritional efficacy, making the milk more beneficial for various consumer needs. This optimization technique not only improves the quality of dairy products but also supports broader nutritional objectives, making it a valuable addition to food science and nutrition technologies. The illustrations in FIG. 5E and FIG. 5F provide empirical evidence of the algorithm's capability to refine and enhance the amino acid profiles of widely consumed dairy products like cow's milk. The clear, quantifiable improvements demonstrated in these figures reinforce the patent's utility and innovativeness, highlighting its potential impact on the dairy industry and consumer health. The illustrations on FIGS. 5E and 5F may be displayed on the display (similar to as shown in FIGS. 2A and 2B) so that a user can easily compare the improvement of the protein sample if the amino acids suggested to be added are added to the sample.

The present disclosure relates to a detailed amino acid profile 600 of various protein samples, as illustrated in FIGS. 6A and 6B, which delineate the quantification and optimization of amino acids in protein powder 602, peanuts 604, and cow's milk 606. Each of these profiles is organized to show the amino acid contents in descending order and highlights the specific implementation of supplementary regression target (SRT) values 608 for the last four amino acids in each profile.

Referring to FIG. 6A, the amino acid profile for a protein powder sample, designated as "O.N.-GS1000" lists major amino acids including Glutamic Acid at 15.12 grams, Aspartic Acid at 9.49 grams, and Leucine at 8.98 grams. This profile proceeds to list additional amino acids such as Lysine, Threonine, Isoleucine, Proline, Valine, Alanine, Serine, Phenylalanine, Tyrosine, and Tryptophan, in decreasing quantities. The SRT values, critical to the understanding of amino acid optimization, include Arginine (1.92 grams, 3.00% slope), Cysteine (1.89 grams, 22.00% slope), Methionine (1.67 grams, 13.00% slope), and Histidine (1.54 grams, 2.00% slope), with Glycine listed as a reference low-abundance amino acid (RLAA) at 1.52 grams. Collectively, these SRT amino acids represent approximately 27% of the total 18-amino acid profile of the protein powder, providing a basis for targeted nutritional enhancements.

The amino acid profile for peanuts reveals a different pattern, with Aspartic Acid leading at 9.71 grams, followed by significant amounts of Glutamic Acid and Tryptophan. This profile includes Leucine, Arginine, Lysine, Valine, Serine, and Isoleucine, among others, with notable SRT values for Histidine (2.82 grams, 4.50% slope), Alanine (2.78 grams, 44.00% slope), Methionine (2.34 grams, 21.50% slope), and Proline (2.12 grams, 47.50% slope), demonstrating a focus on optimizing specific amino acids that are pivotal for enhancing the peanut protein's functional properties. In the case of cow's milk, the amino acid profile is similarly detailed, featuring Glutamic Acid at 12.96 grams and continuing with high concentrations of Leucine, Proline, and Lysine. Lesser, but still significant, quantities include Aspartic Acid, Valine, Isoleucine, Serine, Tyrosine, Phenylalanine, and Threonine. The SRT values for cow's milk emphasize the strategic enhancement of Methionine (2.11 grams, 84.00% slope), Histidine (2.29 grams, 18.00% slope), Tryptophan (1.27 grams, 7.00% slope), and Glycine (1.20 grams, 54.00% slope), with the aim of improving the milk's nutritional value for diverse applications. These comprehensive amino acid profiles, as set forth in FIG. 6A, illustrate a systematic approach to modifying protein sources through precise amino acid supplementation. This methodology significantly improves the nutritional quality of protein samples and offers a substantial advancement over prior art, providing tailored dietary solutions with enhanced functional properties.

FIG. 6B presents an adjusted amino acid profile 620 for various protein samples, including the protein powder 621, peanuts 622, and cow's milk 624. The table details the quantities of various amino acids for each protein sample in descending order, with the last four amino acids categorized as SRT values 626. For the protein powder sample labeled as "O.N.-GS1000", the table lists the amino acid values in grams along with their SRT slopes. Specifically, the amino acids present include Glutamic Acid at 15.12 grams, Aspartic Acid at 9.49 grams, and Leucine at 8.98 grams. Following these, the profile includes Lysine at 8.09 grams, Threonine at 5.94 grams, Isoleucine at 5.73 grams, Proline at 4.97 grams, Valine at 4.74 grams, Alanine at 3.96 grams, Serine at 3.90 grams, Phenylalanine at 2.60 grams, Tyrosine at 2.53 grams, and Tryptophan at 1.92 grams. The SRT amino acids for this sample include Arginine at 1.92 grams with a slope of 0.00%, Cysteine at 1.92 grams with a slope of 2.00%, Methionine at 1.90 grams with a slope of 1.00%, and Histidine at 1.89 grams with a slope of 3.00%. Glycine is listed under the RLAAs category at 1.86 grams. Collectively, these SRT amino acids represent approximately 27% of the total 18-amino acid profile, with a total addition of 0.95 grams per 100 grams of the protein powder.

For the peanut sample, the amino acid profile begins with Aspartic Acid at 9.71 grams, followed by Glutamic Acid at 7.15 grams and Tryptophan at 7.12 grams. The profile continues with Leucine at 7.03 grams, Arginine at 5.62 grams, Lysine at 5.25 grams, Valine at 5.08 grams, Serine at 5.04 grams, Isoleucine at 4.77 grams, Tyrosine at 3.87 grams, Phenylalanine at 3.79 grams, Threonine at 3.12 grams, and Glycine at 2.96 grams. The SRT values for peanuts include Histidine at 2.82 grams with a slope of 0.00%, Alanine at 2.82 grams with a slope of 2.00%, Methionine at 2.80 grams with a slope of 4.00%, and Proline at 2.76 grams with a slope of 2.00%. Cysteine is listed at 2.74 grams, contributing to a total addition of 2.25 grams per 100 grams of peanuts. In the case of cow's milk, the amino acid profile includes Glutamic Acid at 12.96 grams, Leucine at 7.20 grams, Proline at 7.08 grams, and Lysine at 6.64 grams. The profile also lists Aspartic Acid at 5.58 grams, Valine at 4.86 grams, Isoleucine at 4.81 grams, Serine at 4.74 grams, Tyrosine at 4.68 grams, Phenylalanine at 4.46 grams, Threonine at 3.90 grams, Arginine at 3.11 grams, and Alanine at 2.50 grams. The SRT amino acids for cow's milk include Histidine at 2.29 grams with a slope of 0.00%, Methionine at 2.29 grams with a slope of 3.00%, Tryptophan at 2.26 grams with a slope of 2.00%, and Glycine at 2.24 grams with a slope of 3.00%. Cysteine is listed at 2.21 grams, leading to a total addition of 3.76 grams per 100 grams of cow's milk. These SRT values for each protein sample highlight the importance of specific amino acids in adjusting and optimizing the amino acid profiles, contributing to enhanced nutritional and functional properties of the protein samples.

In the disclosed embodiments, reference is made to FIGS. 6A and 6B, which detail the quantitative amendments in the amino acid profiles of protein samples by delineating the specific quantities of the amino acids Cysteine, Methionine, Histidine, and Glycine added thereto. Notably, FIG. 6B discloses a cumulative addition of 3.76 grams of these amino acids to a baseline quantity of 100 grams of the protein sample, representing an enhancement beyond the intrinsic amino acid composition. This augmentation is computed as the aggregate difference between the concentrations in an adjusted amino acid profile and those in the original amino acid profile of the sample.

Illustratively, the adjusted amino acid profile for Tryptophan in cow's milk is noted at 2.26 grams in FIG. 6B as opposed to the 1.27 grams in the unmodified profile of FIG. 6A, reflecting a net increase of 0.99 grams. In a like manner, the concentration of Methionine escalates modestly from 2.11 to 2.29 grams, providing a differential of 0.18 grams. Further increments are observed with Glycine and Cysteine, where the increases are recorded at 1.04 and 1.55 grams, respectively, summing to the total enhanced weight of 3.76 grams. These updated values of the SRT may be displayed on a display transmitted to the user on the first user device, similar to the GUI 235 displayed on the first user device of FIG. 2C for the protein sample peanuts.

The differential values serve as a guideline for the precise addition of amino acids to the protein sample. This method ensures that the total quantity of amino acids incorporated does not surpass the calculated threshold of 3.76 grams. Typically, the enhancement involves micro-additions ranging from 1 to 2 grams per amino acid, facilitating the tailored optimization of the amino acid profiles of diverse protein samples. Such specificity in modification permits the adjustment of caloric content contributed by the added amino acids, as evidenced in FIG. 6B. Depending on the protein sample, the additional amino acid content can vary, such as a mere 0.95 grams in one instance, contrasted with a more substantial addition of 3.76 grams in another, the latter correlating with a higher caloric increment.

This innovative method markedly advances the nutritional and functional quality of protein samples. By enabling the precise calibration of amino acid additions, the invention enhances the suitability of protein samples for varied dietary requirements and application-specific functionalities, presenting a significant improvement over the prior art. This system not only offers a refined approach to protein supplementation but also contributes to the broader utility of dietary proteins in nutritional science and food technology.

Figure 7:
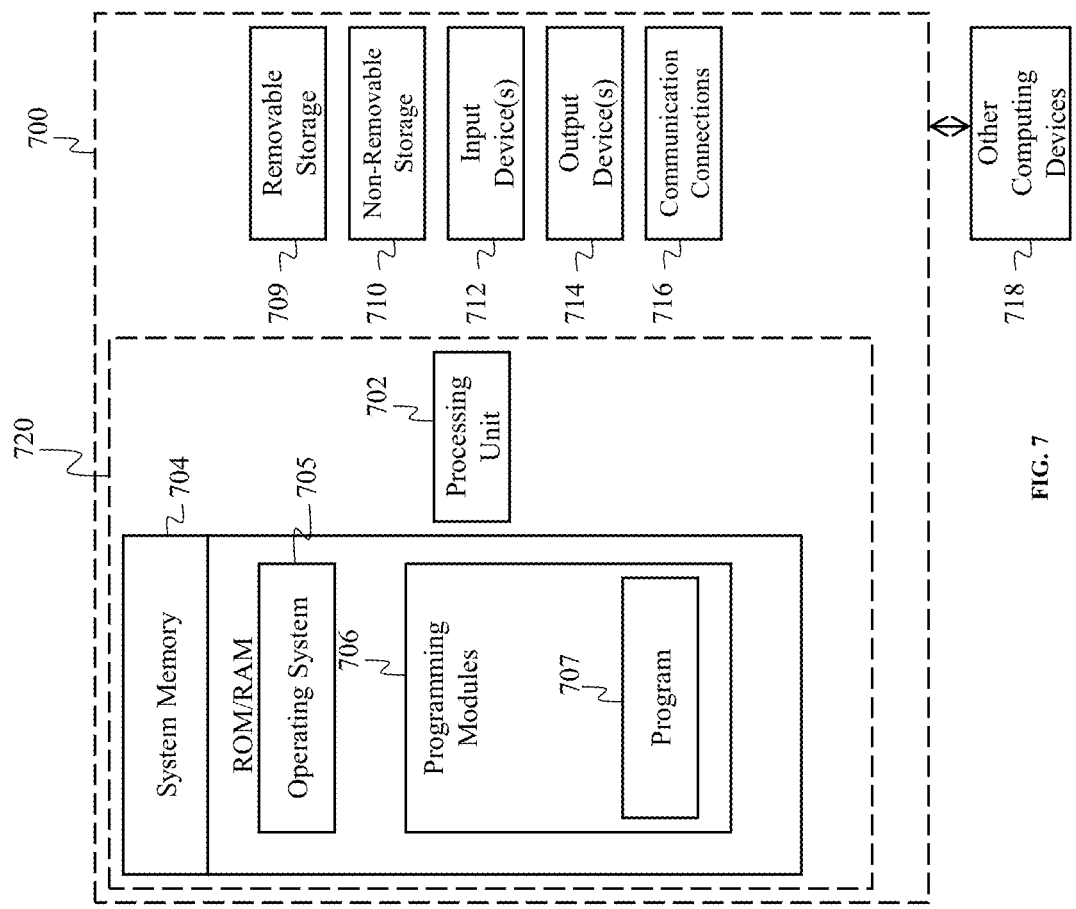
FIG. 7 is a block diagram of a system including a computing device and other computing devices, according to an example embodiment.

Referring now to FIG. 7, a block diagram of a system including an example computing device 700 and other computing devices is shown, according to an exemplary embodiment of present technology. Consistent with the embodiments described herein, the aforementioned actions performed by the processor may be implemented in a computing device, such as the computing device 700 of FIG. 7. Any suitable combination of hardware, software, or firmware may be used to implement the computing device 700. The aforementioned system, device, and processors are examples and other systems, devices, and processors may comprise the aforementioned computing device. Furthermore, computing device 700 may comprise an operating environment for computing device 700 and methods 400, 450 and other described herein. Methods 400, and 450 and others described herein may operate in other environments and are not limited to computing device 700.

With reference to FIG. 7, a system consistent with an embodiment of the invention may include a plurality of computing devices, such as computing device 700. In a basic configuration, computing device 700 may include at least one processing unit 702 and a system memory 704. In addition, computing device 700 may include at least one graphics processing unit (GPU) 703 to render images and videos quickly and efficiently. It accelerates graphics processing, offloads tasks from the processing unit 702, and enables real-time interactivity and high-quality visuals in applications. Depending on the configuration and type of computing device, system memory 704 may comprise, but is not limited to, volatile (e.g., random access memory (RAM)), non-volatile (e.g., read-only memory (ROM)), flash memory, or any combination or memory. System memory 704 may include operating system 705, and one or more programming modules 706. Operating system 705, for example, may be suitable for controlling computing device 700's operation. In one embodiment, programming modules 706 may include, for example, a program module 707 for executing the actions of the portable detector, for example. Furthermore, embodiments of the invention may be practiced in conjunction with a graphics library, other operating systems, or any other application program and is not limited to any particular application or system. This basic configuration is illustrated in FIG. 7 by those components within a dashed line 720.

Computing device 700 may have additional features or functionality. For example, computing device 700 may also include additional data storage devices (removable and/or non-removable) such as, for example, magnetic disks, optical disks, or tape. Such additional storage is illustrated in FIG. 7 by a removable storage 709 and a non-removable storage 710. Computer storage media may include volatile and nonvolatile, removable and non-removable media implemented in any method or technology for storage of information, such as computer readable instructions, data structures, program modules, or other data. System memory 704, removable storage 709, and non-removable storage 710 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 700. Any such computer storage media may be part of computing device 700. Computing device 700 may also have input device(s) 712 such as a keyboard, a mouse, a pen, a sound input device, a camera, a touch input device, etc. Output device(s) 714 such as a display, speakers, a printer, etc. may also be included. The aforementioned devices are only examples, and other devices may be added or substituted.

Computing device 700 may also contain a communication connection 716 that may allow computing device 700 to communicate with other computing devices 718, such as over a network in a distributed computing environment, for example, an intranet or the Internet. Communication connection 716 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, Bluetooth® and other wireless media. The term computer readable media as used herein may include both computer storage media and communication media.

As stated above, a number of program modules and data files may be stored in system memory 704, including operating system 705. While executing on processing unit 702, programming modules 706 (e.g., program module 707) may perform processes including, for example, one or more of the stages of the methods 400 and 450 as described above. The aforementioned processes are examples, and processing unit 702 may perform other processes. Other programming modules that may be used in accordance with embodiments of the present invention may include electronic mail and contacts applications, word processing applications, spreadsheet applications, database applications, slide presentation applications, drawing or computer-aided application programs, etc.

Generally, consistent with embodiments of the invention, program modules may include routines, programs, components, data structures, and other types of structures that may perform particular tasks or that may implement particular abstract data types. Moreover, embodiments of the invention may be practiced with other computer system configurations, including hand-held devices, multiprocessor systems, microprocessor-based or programmable user electronics, minicomputers, mainframe computers, and the like. Embodiments of the invention may also be practiced in distributed computing environments where tasks are performed by remote processing devices that are linked through a communications network. In a distributed computing environment, program modules may be located in both local and remote memory storage devices.

Furthermore, embodiments of the invention may be practiced in an electrical circuit comprising discrete electronic elements, packaged or integrated electronic chips containing logic gates, a circuit utilizing a microprocessor, or on a single chip (such as a System on Chip) containing electronic elements or microprocessors. Embodiments of the invention may also be practiced using other technologies capable of performing logical operations such as, for example, AND, OR, and NOT, including but not limited to mechanical, optical, fluidic, and quantum technologies. In addition, embodiments of the invention may be practiced within a general-purpose computer or in any other circuits or systems.

Embodiments of the present invention, for example, are described above with reference to block diagrams and/or operational illustrations of methods, systems, and computer program products according to embodiments of the invention. It is understood that, in certain embodiments, the functions/acts noted in the blocks may occur out of order as shown in any flowchart. For example, two blocks shown in succession may in fact be executed substantially concurrently or the blocks may sometimes be executed in the reverse order, depending upon the functionality/acts involved.

While certain embodiments of the invention have been described, other embodiments may exist. Furthermore, although embodiments of the present invention have been described as being associated with data stored in memory and other storage mediums, data can also be stored on or read from other types of computer-readable media, such as secondary storage devices, like hard disks, floppy disks, or a CD-ROM, or other forms of RAM or ROM. Further, the disclosed methods' stages may be modified in any manner, including by reordering stages and/or inserting or deleting stages, without departing from the invention.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. It should also be noted that additional information about the attached methods and systems is included in the appendix to this specification, the substance of which Application hereby incorporated by reference.

The invention claimed is:

1. A method for increasing, for a gram of protein, muscle protein synthesis (MPS) relative to another nitrogenous process:
  a) obtaining, from a computing device, an amino acid profile of a protein sample comprising a plurality of amino acids, wherein each of the plurality of amino acids comprise a value measured in grams and wherein the value of the plurality of amino acids are sorted from greatest to least;
  b) plotting, using a server, each of the plurality of amino acids, on a two-dimensional graph, in descending order based respective values so as to identify a final five data points of the amino acid profile to define a slope regression tail;
  c) calculating, using the server, an initial slope value for each of the final five data points, wherein the initial slope value is defined as $M=(Y2-Y1)/(X2-X1)$, with Y representing each value for each of the final five data points and X representing, in the descending order, each of the final five data points; and
  d) adjusting, using the server, the amino acid profile algorithmically to generate an adjusted amino acid profile, by:
    calculating, for each of the final five data points, a percent difference between a highest initial slope values and each of the final five data points of the slope regression tail;
    multiplying the percent difference by each respective initial slope value to yield a product for each of the final five data points;
    adding the product back to the value of a respective amino acid to yield a corrected weight for each of the final five data points; and
    for a lowest three amino acids of the plurality of amino acids of the slope regression tail, adding a correction score of 1%, 2%, and 3% respectively, by multiplying the corrected weight for each of the lowest three amino acids by the correction score and then subtracting that correction value from the corrected weight.

2. The method of claim 1, wherein an x-axis defines each of the plurality of amino acids in the descending order.

3. The method of claim 2, wherein a y-axis is defined as gram of amino acid per 100 grams of sample.

4. The method of claim 1, wherein the method further comprises adjusting, using the server, the protein sample by adding to the protein sample at least one additive amino acid from the plurality of amino acids that define the slope regression tail.

5. The method of claim 4, wherein the method further comprises:
  transmitting, to the computing device, a message such that the computing device displays on a display a first graphical representation displaying the initial slope value for the final five data points that define the slope regression tail; and
  transmitting, to the computing device, a second message such that the computing device displays on a display a second graphical representation displaying an adjusted slope value for an adjusted five data points for the adjusted amino acid profile that define an adjusted slope regression tail.

6. The method of claim 5, further comprising providing the second graphical representation displaying the adjusted slope value to a second computing device associated with a user.

7. A method for increasing, for a gram of protein, muscle protein synthesis (MPS) relative to another nitrogenous process:
  obtaining, from a computing device, an amino acid profile of a protein sample comprising a plurality of amino acids, wherein each of the plurality of amino acids comprise a value measured in grams and wherein the value of the plurality of amino acids are sorted from greatest to least;
  storing, in a connected database, the amino acid profile in a protein sample record;
  executing a program on a server communicable coupled with a communications network, wherein the connected database comprises a plurality of instructions, the program configured for:
    accessing, in the connected database, the amino acid profile from the protein sample record and the plurality of instructions;

plotting, using the server, each of the plurality of amino acids from the amino acid profile, on a two-dimensional graph, in descending order based respective values so as to identify a final five data points of the amino acid profile to define a slope regression tail;

calculating, using the server, an initial slope value for each of final five data points, wherein the initial slope value is defined as $M=(Y2-Y1)/(X2-X1)$, with Y representing each of the final five data points and X representing a position, in the descending order, for each of the final five data points;

adjusting, using the server, the amino acid profile algorithmically to generate an adjusted amino acid profile, by:

calculating, using the server, for each of the final five data points, a percent difference between a highest initial slope values for each of the final five data points of the slope regression tail;

multiplying, using the server, the percent difference by each respective initial slope value to yield a product for each of the final five data points;

adding, using the server, the product back to the value of a respective amino acid to yield a corrected weight for each of the final five data points; and for a lowest three amino acids of the plurality of amino acids of the slope regression tail, adding, using the server, a correction score of 1%, 2%, and 3% respectively, by multiplying the corrected weight for each of the lowest three amino acids by the correction score and then subtracting that correction value from the corrected weight.

8. The method of claim 7 comprising creating, in the connected database, a protein sample record.

9. The method of claim 7, wherein an x-axis defines each of the plurality of amino acids in the descending order, and a y-axis is defined as gram of amino acid per 100 grams of sample.

10. The method of claim 9, wherein the method further comprises adjusting, using the server, the protein sample by adding to the protein sample at least one additive amino acid from the plurality of amino acids that define the slope regression tail.

11. The method of claim 10, wherein the method further comprises:

transmitting, to the computing device, a message such that the computing device displays on a display of the computing device, a first graphical representation displaying the initial slope value for the final five data points that define the slope regression tail; and transmitting, to the computing device, a second message such that the computing device displays on a display of the computing device, a second graphical representation displaying an adjusted slope value for an adjusted five data points for the adjusted amino acid profile that define an adjusted slope regression tail.

12. The method of claim 11, further comprising transmitting, to the computing device, the second message such that the computing device displays on a display of the computing device, the second graphical representation displaying the adjusted slope value to the second computing device associated with a user.

13. A method for increasing, for a gram of protein, muscle protein synthesis (MPS) relative to another nitrogenous process:

obtaining, from a computing device, an amino acid profile of a protein sample comprising a plurality of amino acids, wherein each of the plurality of amino acids comprise a value measured in grams and wherein the value of the plurality of amino acids are sorted from greatest to least;

storing, in a connected database, the amino acid profile in a protein record;

executing a program on a server communicable coupled with a communications network, wherein the connected database comprises a plurality of instructions, the program configured for:

accessing, in the connected database, the amino acid profile from an amino acid record and the plurality of instructions;

identifying, using the server, from the amino acid profile a subset of five target amino acids comprising five lowest values of the amino acid profile;

calculating, using the server, an initial slope value for each of the subset of five target amino acids, wherein an initial slope value is defined as $M=(Y2-Y1)/(X2-X1)$, with Y representing each value for each of five target amino acids and X representing a position, in a descending order for each of target amino acids; and adjusting, using the server, the amino acid profile algorithmically to generate an adjusted amino acid profile, by:

calculating, for each of the target amino acids, a percent difference between (i) a highest initial slope value of initial slope values and (ii) initial slope values of each target amino acids of the plurality of amino acids;

multiplying, for each of the target amino acids, the percent difference by each respective initial slope value to yield a product;

adding, for each of the target amino acids, the product back to the value of target amino acid to yield a corrected weight for each of target amino acids;

for a lowest three of the target amino acids, adding a correction score of 1%, 2%, and 3% respectively, by multiplying the corrected weight for each of the lowest three of the target amino acids by the correction score and then subtracting that correction value from the corrected weight; and transmitting to the computing device a message that causes the computing device to display on a display (i) a first graphical representation displaying on a two dimensional graph the initial slope value for the target amino acids that define a slope regression tail and (ii) a second graphical representation displaying the two dimensional graph an adjusted slope value for an adjusted target amino acids for the adjusted amino acid profile that define an adjusted slope regression tail.

14. The method of claim 13 comprising creating, in the connected database, a protein sample record.

15. The method of claim 13, wherein an x-axis defines each of the target amino acids in the descending order, and a y-axis is defined as gram of amino acid per 100 grams of sample.

16. The method of claim 15, wherein the method further comprises adjusting, using the server, the protein sample by adding to the protein sample at least one additive amino acid from the plurality of amino acids that define the slope regression tail.

17. The method of claim 16, wherein the method further comprises:

transmitting, to the computing device, a message such that the computing device displays on a display of the computing device a first graphical representation displaying the initial slope value for final five data points that define the slope regression tail; and transmitting, to the computing device, second message such that the computing device displays on a display of the computing device a second graphical representation displaying an adjusted slope value for an adjusted five data points for the adjusted amino acid profile that define an adjusted slope regression tail.

18. The method of claim 17 further comprising that the second graphical representation displays the adjusted slope value on the display of the second computing device.

19. The method of claim 18, wherein the amino acid profile is obtained in response to receiving inputs from the computing device associated with amino acid profile of the protein sample on a Graphical User Interface displayed of the computing device.

* * * * *